US008115059B1

(12) United States Patent
Palli et al.

(10) Patent No.: US 8,115,059 B1
(45) Date of Patent: Feb. 14, 2012

(54) GENE EXPRESSION MODULATION SYSTEM FOR USE IN PLANTS AND METHOD FOR MODULATING GENE EXPRESSION IN PLANTS

(75) Inventors: Subba Reddy Palli, Lexington, KY (US); Ajay Kumar Singh, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 152 days.

(21) Appl. No.: 12/683,121

(22) Filed: Jan. 6, 2010

Related U.S. Application Data

(63) Continuation-in-part of application No. 11/491,690, filed on Jul. 24, 2006, now abandoned.

(60) Provisional application No. 60/702,047, filed on Jul. 22, 2005.

(51) Int. Cl.
*C12N 15/82* (2006.01)
*C12N 15/10* (2006.01)
*C12N 15/52* (2006.01)
*C12N 15/62* (2006.01)

(52) U.S. Cl. .................. 800/288; 800/284; 435/320.1; 435/410; 536/23.1; 536/23.2; 536/23.4; 536/23.5

(58) Field of Classification Search .................. None
See application file for complete search history.

(56) References Cited

U.S. PATENT DOCUMENTS

| | | | |
|---|---|---|---|
| 5,880,333 A | 3/1999 | Goff et al. | |
| 6,258,603 B1 | 7/2001 | Carlson et al. | |
| 6,265,173 B1 | 7/2001 | Evans et al. | |
| 6,379,945 B1 | 4/2002 | Jepson et al. | |
| 6,504,082 B1 | 1/2003 | Albertsen et al. | |
| 6,706,470 B2 | 3/2004 | Choo et al. | |
| 2002/0110861 A1 | 8/2002 | Dhakialla et al. | |
| 2002/0119521 A1 | 8/2002 | Palli et al. | |
| 2002/0155540 A1 | 10/2002 | Padidam | |
| 2003/0024006 A1 | 1/2003 | Choo et al. | |
| 2003/0110528 A1 | 6/2003 | Albertsen et al. | |
| 2003/0131381 A1 | 7/2003 | Albertsen et al. | |
| 2003/0154509 A1 | 8/2003 | Pascal et al. | |
| 2003/0211455 A1 | 11/2003 | Tran et al. | |
| 2004/0033600 A1* | 2/2004 | Palli et al. ................. | 435/455 |
| 2004/0049037 A1 | 3/2004 | Tice et al. | |
| 2004/0096942 A1* | 5/2004 | Kapitskaya et al. ........ | 435/69.1 |
| 2004/0197861 A1 | 10/2004 | Palli | |
| 2004/0235097 A1 | 11/2004 | Zhang et al. | |

OTHER PUBLICATIONS

Aoyama, T. and Chua, N. H. (1997) A glucocorticoid-mediated transcriptional induction system transgenic Plant J. 11, 605-612.
Bereterbide, A., Hernould, M., Castera, S. and Mouras, A (2001) Inhibition of cell proliferation, cell expansion and differentiation by the *Arabidopsis* SUPERMAN gene in transgenic tobacco plants. Planta, 214: 22-29.
Bowman, J.L., Sakai, H., Jack, T., Weigel, D., Mayer, U. and Meyerowih, E.M. (1992) SUPERMAN, a regulator of floral horneotic genes in *Arabidopsis*, Development, 114: 599-615.
Bohner, Lenk, I.I., Rieping, M., Herald,M. and Gatz, C (1999) Technical advance: transcriptional activator TGV mediates dexamethasone-inducible and tetracycline-inactivatable gene expression, Plant J. 19, 87-95.
Bruce,W., Folkerts, O., Gamaat, C., Crasta, O., Roth. B. and Bowen, B. (2000) Expression profiling of the maize flavonoid pathway genes controlled by estradiol-inducible transcription factors CRC and P. Plant Cell, 12, 65-80.
Caddick, M.X., Greenland, A.J., Jepson, 1., Krause, K.P., Qu, N., Riddell, K.V., Salter, M., Schuch, W., Sonnewaid U. and Tomsett, A.B. (1998) An ethanol inducible gene switch for plants used to manipulate carbon metabolism. Nat. Biotechnol. 16, 177-180.
Carlson, G.R., Dhadialla, T.S., Hunter, R., Jansson, R.K., Jany, C.S., Lidert, Z. and Slawecki, R.A. (2001) The chemical and biological properties of methoxyfenozide, a new insecticidal ecdysteroid agonist. Pest Manag. Sci. 57, 115-119.
Chen, K., Du, L. and Chen, Z. (2003) Sensitization of defense responses and activation of programmed cell death by a pathogeninduced receptor-like protein kinase in *Arabidopsis*. Plant Mol. Biol. 53,61-74.
Christopherson, K.S., Mark, M.R , Bajai, V. and Godowski, P.J. (1992) Ecdysteroid-dependent regulation of genes in mammalian cells by a *Drosophila* ecdysone receptor and chimeric transactivators. Proc. Natl Acad. Sci, USA, 89, 6314-6318.
Clough. S.J. and Bent, A.F. (1998) Floral dip: a simplified method for Agrobacterium-mediated transformation of *Arabidopsis thaliana*. Plant J. 16,735-743.
Craft, J., Samalova. M. Baroux, C., Townley, H . Martinez, A,. Jepson, I., Tsiantis, M. and Moore, I (2005) New pOpiLhG4 vectors for stringent glucocorticoid-dependent transgene expression in *Arabidopsis*. Plant 3 , 41: 899-918.
De Veylder, L ., Van Montagu lnze M. and Inze, D. (1997) Herbicide safener-inducible gene expression *Arabidopsis thaliana*. Plant Cell Physiol. 38,568-577.
Dey, N. and Maiti, I.B. (1999a) Structure and promoter/leader deletion analysis of *mirabilis* mosaic virus (MMV) full-length transcript promoter in transgenic plants. Plant Mol. Biol. 40,771-782.
Dey, N. and Maiti,I.B. (1999b) Further characterization and expression analysis of *mirabilis* mosaic caulimavirus (MMV) full-length transcript promoter with single and double enhancer domains in transgenic plants. Transgenics, 3, 61-70.
Dhadialla, T.S., Carlson, G.R. and Le, D.P. (1998) New insecticides with ecdysteroidal and juvenile hormone activity. Annu. Rev. Entomol. 43,545-569.
Dinkins, R.D., Pflipsen, C., Thompson, A. and Collins, G.B. (2002) Ectopic expression of an *Arabidopsis* single zinc finger gene in tobacco results in dwarf plants. Plant Cell Physiol., 43: 743-750.
Dinkins. R.D., Pflipsen, C. and Collins, G.B. (2003) Expression and deletion analysis of an *Arabidopsis* SUPERMAN-Like zinc finger gene. Plant Sci., 165: 33-41.

(Continued)

*Primary Examiner* — Brent T Page
(74) *Attorney, Agent, or Firm* — Stites & Harbison PLLC; Mandy Wilson Decker

(57) ABSTRACT

An EcR-based gene expression modulation system for use in plants includes an EcR gene expression cassette, a modified RXR gene expression cassette, and a gene-of-interest expression cassette, which can be expressed in a host plant cell.

37 Claims, 10 Drawing Sheets

OTHER PUBLICATIONS

Getz, C. 1996) Chemically inducible promoters in transgenic plants. Current Opinion Biotechnol 7: 168-172.

Getz, C. and Lenk, I. (1998) Promoters that respond to chemical inducers. Trend Plant Sc. 3, 352-358.

Gatz, C, Frohberg, C. and Wendenburg, R. (1992) Stringent repression and homogeneous de-repression by tetracycline of a modified CaMV 35S promoter in intact transgenic tobacco plants. Plant J. 2, 397-404.

Guo, H.-S., Fei, J.-F., Xie, Q. and Chua, N.H. (2003) A chemicalregulated inducible RNAi system in plants. Plant J. 34, 383-392.

Jepson, I., Lay, V.J., Holt, D.C., Bright, S.W. and Greenland, A.J. (1994) Cloning and characterization maize herbicide safenerinduced cDNAs encoding subunits of glutathione S-transferase isoforms I, II and IV. Plant Mol. Biol. 26, 1855-1866.

Koo, J.C., Asurmendi, S., Bick, J., Woodford-Thomas, T. and Beachy. R.N. (2004) Ecdysone agonist-inducible expression of a coat protein gene from tobacco mosaic virus confers viral resistance in transgenic Arabidopsis. Plant J. 37, 439-448.

Kunkel et al., Nat Biotechnol 17:9 16-9 (1999).

Laufs, et al.,Development 130: 785-796 (2003).

Love, J., Allen, G.C., Gatz, C. and Thompson, W.F. (2002) Differential Top10 promoter regulation by, six tetracycline analogues in plant cells. J. Exp. Bot. 53, 1871-1877.

Maiti, I.B., Gowda, S., Kieman, J., Ghosh, S.K. and Shepherd, R J. (1997) Promoter/leader deletion analysis and plant expression vectors with the figwort mosaic virus (FMV) full length transcript (FLT) promoter containing single of double enhancer domains. Transgenic Res. 6, 143-156.

Martinez, A., Sparks, C., Hart, C.A., Thompson, J. and Jepson, I. (1999a) Ecdysone agonist inducible transcription in transgenic tobacco plants. Plant J. 19, 97-106.

Martinez A., Sparks, C., Drayton, P., Thompson, J., Greenland, A and Jepson, I. (1999b) Creation of ecdysone receptor chimeras in plants for controlled regulation of gene expression, Mol. Gen. Genet. 261, 546-552.

Martinez. A., Scanlon, D., Gross, B., Perara, S.C., Palli. S.R , Greenland, A.J., Windass, J., Pongs, O., Broad, P. and Jepson, I. (1999c) Transcriptional activation of the cloned *Heliothis virescens* (Lepidoptera) ecdysone receptor (HvEcR) by muristeroneA. Insect Biochem. Moi. Biol, 29, 915-930.

McNellis et al., Plant 14:247-57 (1998).

Mett, V.L. , Lochhead, L.P. and Reynolds, P.H. (1993) Copper-controllable gene expression system for whole plants. Proc. Natl. Acad. Sci USA, 90, 4567-4571.

Morrison, T.B., Weis, J. J. and Wittwer, C.T. (1998) Quantification of low-copy transcripts by continuous SYBR Green I monitoring during amplification. Biotechniques, 24: 954-958,960,962.

No, D., Yac, T.P. and Evans, R.M. (1996) Ecdysone-inducible gene expression in mammalian and transgenic mice. Proc. Natl Acad. Sci. USA, 93, 3346-3351.

Odell. T., Nagy, F. and Chua, N.H. (1985) identification of DNA sequences required for activity of the cauliflower mosaic virus 35S promoter. Nature, 313, 810-812.

Padidam, M. (2003) Chemically regulated gene expression in plants. Curr. Opin. Plant Biol. 6, 169-177.

Padidam, M., Gore. M., Lu, D.L. and Smirnova, O. (2003) Chemicalinducible, ecdysone receptor-based gene expression system for plants. Transgenic Res. 12, 101-109.

Palli, S,R. (2005) Gene switches for regulation of biopesticide genes. Biopesticide Int., in press.

Palli, S.R., Kapitskaya, M.Z., Kumar, M.B. and Cress, D.E. (2003) Improved ecdysone receptor-based inducible gene regulation system. Eur. J. Biochem 270, 1308-1315.

Payne. T., Johnson, S.D. and Kolhinow, A.M. (2004) Knuckles (KNU) encodes a C2H2 zinc-finger protein that regulates development of basal pattern elements of the *Arabidopsis gynoecium*, Development, 131: 3737-3749.

Perera, S.C., Palli, S.R., Ladd, T R., Krell, P.J. and Retnakaran, A. (1998) The ultraspirade gene of the spruce budworm, *Choristoneura fumiferana*: cloning of cDNA and developmental expression of mRNA. Dev. Genet. 22, 169-179.

Ririe, KM., Rasmussen, R.P. and Wittwer, C.T. (1997) Product differentiation by analysis of DNA melting curves during the polymerase chain reaction. Anal Biochem., 245: 154160.

Roslan, H.A. Salter, M.G., Wood, C.D. et al. (2001) Characterization of the ethanol-inducible alc gene-expression system in *Arabidopsis thaliana*. Plant J. 28,225-235.

Saez, E., No, D., West, A. and Evans, R.M. (1997) Inducible gene expression in mammalian cells and transgenic mice. Curr. Opin. Biotechnol. 8, 608-616.

Sakai, H., Medrano, L,J. and Meyerowitz, E.M. (1995) Role of SUPERMAN in maintaining *Arabidopsis floral whorl* boundaries. Nature 378: 199-203.

Samalova, M., Brzobohaty, B, and Moore, I. (2005) pOp61LhGR: a stringently regulated and highly responsive dexamethasone-inducible gene expression system for tobacco. Plant J., 41: 919-935.

Schardl, C. L., Byrd. A.D., Benzion, G., Altschuler, M.A., Hildebrand, D.F and Hunt, A.G. (1987) Design and construction of a versatile system for the expression of foreign genes in plants. Gene, 61,1-11.

Schena, M., Lloyd, A.M. and Davis, R.W. (1991) A steroid-inducible gene expression system for plant cells. Proc. Natl Acad. Sci. USA, 88, 10421-10425.

Severin, K. and Schoffl, F. (1990) Heat-inducible hygromycin resistance in transgenic tobacco. Plant Mol. Biol. 15, 827-833.

Suehara, K.-I, Takao, S., Nakamura, K., Uozumi, N. and Kobayashi, T. (1996) Optimal expression of GUS gene from methyl jasmonate-inducible promoter in high density cultures of transformed tobacco cell line BY2. J. Ferm. Bioeng. 62,51-55.

Takeda, S., Matsumoto, N. and Okada, K., (2004) Rabbit Ears, encoding a SUPERMAN-like zinc finger protein, regulates petal development in *Arabidopsis thaliana*. Development, 131: 425-434.

Tang, W., Luo, X. and Samuels, V. (2004) Regulated gene expression with promoters responding to inducers. Plant Sci. 166, 827-834.

Tavva, V., Dinkins, R., Palli, S., and Collins, G. (2006) Development of a methoxyfenozide-responsive gene switch for applications in plants, Plant J. 45, 457-469.

Unger, E., Olgan, A.M., Trimnell, M., Xu, R.J., Kendall, T., Roth, B. and Albertsen, M. (2002) A chimeric ecdysone receptor facilitates methoxyfenozide-dependent restoration of male fertility in mis45 maize Transgenic Res. 11, 455-465.

Wang, H. and Negishi, M. (2003) Transcriptional regulation of cytochrome p450 2B genes by nuclear receptors. Curr. Drug. Metab 4, 515-525.

Weinmann, P., Gossen, M., Hillen, W., Bujard, H. and Gatz, C., (1994) A chimeric transactivator allows tetracycline-responsive gene expression in whole plants. Plant M. 5, 559-569.

Williams, S., Friedrich, L., Dincher, S., Carozzi, N. and Kessmann, H. (1992) Chemical regulation of *Bacillus* thuringiensis-endotoxin expression in transgenic plants. BioTechnology, 10, 540-543.

Wirtz, E. and Clayton, C. (1995) Inducible gene expression in trypanosomes mediated by a prokaryotic repressor. Science, 268, 1179-1183.

Yoshizumi et al. Plant Cell 11: 1883-96 (1999).

Zhang, J.2. (2003) Overexpression analysis of plant transcription factors. Curr Opin Plant Biol., 6: 430-440.

Zuo, J. and Chua, N.H. (2000) Chemical-inducible systems for regulated expression of plant genes. Curr. Opin. Biotechnol. 11, 146-151.

Zuo, J., Niu, Q.W. and Chua, N.H. (2000) Technical advance: an estrogen receptor-based transactivator XVE mediates highly inducible gene expression in transgenic plants. Plant J. 24, 266-273.

* cited by examiner

GENE EXPRESSION MODULATION SYSTEM FOR USE IN PLANTS AND METHOD FOR MODULATING GENE EXPRESSION IN PLANTS

RELATED APPLICATIONS

This application is a continuation-in-part of U.S. patent application Ser. No. 11/491,690 filed Jul. 24, 2006 now abandoned, which is incorporated herein by this reference. U.S. patent application Ser. No. 11/461,690 claims priority to U.S. Provisional Patent Application Ser. No. 60/702,047 filed on Jul. 22, 2005, which is also incorporated herein by this reference.

TECHNICAL FIELD

The present invention relates to the field of gene expression, and, more particularly, to chemically-inducible systems that activate or inactivate gene expression in host plant cells.

INTRODUCTION

A gene switch is a chemically inducible system that activates or inactivates gene expression in host cells. Generally, gene switches, or gene regulation systems, are based on the interaction of a chemical inducer with specifically designed receptors or transcription factors. Such gene regulation systems generally have two transcription units and regulate a target gene in the following manner. The product of the first transcription unit is a transcription factor (activator or repressor protein), which is synthesized under the control of a particular promoter, e.g., cell-specific, tissue-specific, developmental-stage-specific promoter, to provide additional control. The second transcription unit includes a target promoter containing a response element sequence to which the transcription factor (activator or repressor protein) binds to activate or repress the expression of the target gene. An optimal gene regulation system should have low or no basal expression in the absence of an inducer or ligand, and high induced expression in the presence of a wide range of inducer or ligand concentrations. Also, an ideal system should involve a non-toxic inducer that can be easily applied, that is effective at low levels, and that is specific to the gene of interest.

Gene switches have a wide range of uses. Over and under expression of genes can be accomplished using chemically-inducible gene switches. For example, the glucocorticoid receptor (GR)-based switch was used for dexamethasone-inducible expression of bacterial avrRpt2 avirulence gene. Treatment of transgenic plants with dexamethasone led to cell-death response. See McNellis et al., Plant J 14:247-57 (1998).

Chemically-inducible gene switches also have utility in functional genomic applications, e.g., investigating gene function. For example, some plant genes that cause lethality at the early stages of development (e.g. Embryogenesis) may also play important roles at later stages of development. Mutations in such genes may lead to lethality at the early stages of development and make it impossible to study their function in later stages of development. However, it is possible to introduce the appropriate coding sequence for a given mutation under the control of a gene switch that, in the presence of an inducer at the early stages of development, will allow plants to develop. Withdrawal of the inducer, at later stages of development, will allow studies on functions of these genes. For example, in Arabidopsis, the unusual floral organs (UFO) gene is required for floral development. Use of ethanol-inducible expression system to study the role of UFO by ubiquitously expressing it in ufo loss-of-function flowers at different developmental stages and for various lengths of time has allowed floral phenotypes that were not observed in loss-of-function backgrounds to be found. See Laufs, et al., Development 130: 785-796 (2003).

Conditional regulation of transgene expression by the interaction of a chemical inducer with a designed receptor or transcription factor is a powerful tool for determination of gene function and also for plant biotechnological applications (Aoyama and Chua, 1997; Koo et al. 2004; Martinez et al. 1999; Padidam et al. 2003; Saez et al. 1997; Wiaz and Clayton, 1995). The precise timing and control of gene expression are important aspects of chemically inducible gene regulation systems.

The selective induction of gene expression is typically accomplished through the use of a promoter whose transcriptional activity is determined by the presence or absence of a specific inducer. By allowing the time and location of gene expression to be precisely regulated, gene switches or inducible promoters may control the deleterious and/or abnormal effects caused by over-expression, or under-expression, of genes and facilitate the understanding of gene function.

Gene switches can also be used for identification of downstream target genes. For example, an estrogen receptor (ER) gene switch has been used to regulate two transcription factors involved in flavonoid pathway for identification of a number of a downstream target gene. See Bruce et al. Plant Cell 12:65-80 (2000).

Gene switches can also be used for expression of antisense strands of genes for co-suppression studies. For example, an antisense strand of Arabiclopsis CDC2b gene was expressed under the control of a GR-based switch. In transgenic plants induction of antisense RNA by dexamethazone resulted in short hypocotyls and open cotyledons. See Yoshizumi et al. Plant Cell 11: 1883-96 (1999). Gene switches are also useful for the control of double stranded RNA production in gene suppression applications using RNAi.

Gene switches can also be used for selection of transgenic plants without the use of herbicides or antibiotics. Due to public concerns over the use of antibiotic or herbicide resistance genes in transgenic plants and concerns over decrease in transformation efficiency due to effect of herbicides and antibiotics on the growth and regeneration of transformed cells, the production of marker-free transgenic plants has become a major objective for plant biologists. For example, a GR-based gene switch was used in this manner to over express the isopentenyltransferase (ipt) gene from the Ti-plasmid of *Agrobacterium tumefaciens*, which led to an increase in generation of shoots from transformed plant cells in the presence of dexamethasone and the shoots developed into normal plants after withdrawal of ligand. See Kunkel et al., Nat Biotechnol 17:9 16-9 (1999).

Gene switches can also be used for efficient spatial and temporal regulated expression of genes for pest resistance, herbicide resistance and trait improvement. For example, an ecdysone receptor (EcR)-based gene switch was used to restore male fertility in maize. Ms45 maize gene that regulates microspore development was placed under the control of EcR-based switch and introduced into ms45 mutant. A non-steroidal agonist, methoxyfenozide was able to restore male fertility in these transgenic plants. See Unger et al. Transgenic Res 11:455-65.

Conditional gene regulation systems, based on the interaction of a chemical inducer with a specifically designed receptor or transcription factor, have been developed and tested in various plants and have proved powerful tools for basic research. However, the ligands that are often used are inappropriate for field use; thus, they have little practical applicability in agriculture. Gene switches developed for use in plants have been reviewed by Tang et al. Plant Science 166: 827-834 and Padidam, Curr Opin Plant Bio 16: 169-77.

Several chemical inducible gene regulation systems, or gene switches have been developed that respond to a variety of chemicals (Gatz et al, 1992; Wilde et al. 1992; Williams et al. 1992; Mett et al. 1993; Rieping et at 1994; Weinmann et al. 1994; Aoyama and Chua 1997; Caddick et al. 1998; Bohner et al. 1999; Martinez et al. 1999a,b; Bruce et al. 2000, Zuo et al. 2000; Padidam et al. 2003). Most of the systems are induced by compounds which are not suitable for agriculture use. To overcome these problems, a more versatile chemical inducible gene regulation system has been developed (Martinez et al. 1999 a,b; Padidam et al. 2003; Unger et al. 2002). The EcR-based gene regulation system is one of the best gene switch available because the chemical ligand required for its regulation, tubefenozide and methoxyfenozide, are already registered for field use (see Palli et al. 2005a for recent reviews).

The advantages and/or disadvantages associated with various chemically inducible gene switches that have been developed to date have been discussed in recent reviews (Padidam 2003; Palli 2005; Tang et al. 2004; Wang and Negishi 2003, Zuo and Chua 2000).

A chemical inducible gene regulation system that specifically regulates transgene expression in response to an exogenous inducer at a particular stage of plant development or in a specific organ is very valuable when using transgene whose constitutive over expression is likely to compromise plant viability or fertility. In addition, gene switches are also useful in reducing the environmental concerns such as gene pollution and antibiotic resistance development associated with genetically modified crops (Hare and Chua 2002; Palli 2005; Palli et al. 2005a).

An ideal chemically inducible gene regulation system should support undetectable level of transgene expression in the absence of a chemical ligand followed by rapid and robust induction of transgene expression in the presence of low concentration (nanomolar) of a chemical ligand. In an effort to find an optimal gene switch, several approaches have been tried (Ainley and Key 1990; Schena et at 1991; Gatz et al. 1992; Mett et al. 1993; Lloyd et al. 1994; Weinmann et al. 1994; Aoyama and Chua 1997; Bruce et al. 2000; Zuo et al. 2000).

Ecdysone receptor (EcR)-based gene switches are desirable because the chemical ligands required for its regulation, tubefenozide and methoxyfenozide, are already registered for field use. Several ligand-binding domains from EcR of *Drosophila melanogaster, Heliothis virescens, Ostrina nubilalis* and *Choristoneura fumiferana* have been used to create EcR-based gene regulation systems or switches. See e.g., Martinez et al. Plant J 19:97-106 (1999); Martinez et al. Mol. Gen. Genet. 261546-552 (1999); Unger et al. Transgenic Res 11:455-465 (2002).

Most known EcR-based gene switches developed for plants require ligand concentrations in the μM levels for activation, which creates a limitation to the use of the gene switch for large-scale agricultural applications. See e.g., Unger et al. Transgenic Res 1 1:455-465 (2002); and Padidam et al., Transgenic Res 12:101-109 (2003); and Koo et al. Plant J37: 439-448 (2004). Additionally, certain EcR-based gene switches that use an ultra spiracle receptor (USP) as a partner and have been shown to work in plants are "leaky" in that they have a high background activity in the absence of ligand. See U.S. Pat. Nos. 6,504,082; 5,880,333 and U.S. Publication Nos. 2003/0131381; 2003/10110528; 2002/0155540.

An EcR gene switch with a potential for use in large-scale field applications and its applicability to a variety of plant species has been developed by adopting a two-hybrid format (Tavva et al. 2006). An EcR gene switch that uses CH9 as partner of CfEcR which shows low background activity in the absence of ligand and high induction of luciferase reporter gene in the presence of nanomolar concentration of methoxyfenozide ligand (Tavva et al. 2006). Use of CH9 having 1-8 helices HsRXR has associated biosafety and social acceptance issues.

Accordingly, there remains a need in the art for a gene switch that can be used in host plant cells that has low or no basal expression in the absence of a ligand, has induced expression in the presence of a wide range of ligand concentrations, and avoids biosafety and social acceptance issues.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently-disclosed subject matter includes an ecdysone receptor (EcR)-based gene expression modulation system for use in plants, which has a two-hybrid format and makes use of a modified retinoid x receptor (RXR) as a partner. The gene switch of the present invention has various utilities in plants. In this regard, the invention further a method of modulating gene expression in a host plant cell, which is useful, for example, to investigate gene function or to select predetermined plants in an agricultural setting without the use of herbicides and/or pesticides.

The EcR-modified RXR gene switch has little or no basal expression in the absence of a ligand, works with a wide range of concentrations, including nM concentrations of ligand, and works in a variety of plant species. Additionally, the EcR-modified RXR gene switch works with ligands that are already registered for field use and are easily applied, making the gene switch useful for large-scale field applications.

The presently-disclosed subject matter includes a system for modulating expression of a gene-of-interest in a host plant cell. In some embodiments, the system can include an EcR gene expression cassette comprising a first polynucleotide encoding a first polypeptide; a modified RXR gene expression cassette comprising a second polynucleotide encoding a second polypeptide; and a gene-of-interest expression cassette for expressing the gene-of-interest in the host plant cell.

The first polypeptide expressed by the EcR gene expression cassette can include a DNA binding domain that recognizes a response element of the gene of interest expression cassette; and a ligand binding domain from an EcR.

The second polypeptide expressed by the modified RXR gene expression cassette can include a transactivation domain for activating a promoter of the gene of interest expression cassette, and; and a ligand binding domain of a modified RXR, comprising a polypeptide sequence of SEQ ID NO: 1 with at least one amino acid mutation.

The first and second polypeptides dimerize in the presence of a ligand. The DNA binding domain binds the response element of the gene-of-interest expression cassette, while the promoter of the gene-of-interest expression cassette is activated by the transactivation domain. As such, when the first and second polypeptides dimerize, expression of the gene-of-interest is affected in the host plant cell.

In some embodiments of the system, the EcR ligand binding domain is a truncated EcR ligand binding domain. In some embodiments of the system, the EcR ligand binding domain is complete and can contain twelve helices. In some embodiments of the system, the ligand binding domain of the EcR is a ligand binding domain selected from: a spruce budworm EcR, a moth EcR, a butterfly EcR, a fly EcR, a mosquito EcR, a beetle EcR, a locust EcR, a whitefly EcR, a fruit fly EcR, a hone bee EcR, and a leafhopper EcR. In some embodiments of the system, the ligand binding domain of the EcR is from a spruce budworm EcR.

In some embodiments of the system, the DNA-binding domain and the response element are selected from: GAL4 147 DNA-binding domain and response element; GAL4 65 DNA-binding domain and response element; GAL4 93 DNA-binding domain and response element; LexA DNA-binding domain and response element; and Lac repressor DNA-binding domain and response element. In some embodiments of the system, the DNA-binding domain and the response element are GAL4 147 DNA-binding domain and response element.

In some embodiments of the system, the at least one amino acid mutation of the modified RXR is selected from the group consisting of: S122A; A105S; T94A; T81H; A62S; A62S:T81H; and A62S:T81H:V123I. In some embodiments of the system, the RXR is a truncated RXR. In some embodiments, the RXR includes 1-12 helices. In some embodiments, the modified RXR includes RXR from different species. In some embodiments, the modified RXR includes RXR from a single species. In some embodiments, the ligand binding domain of the RXR is a ligand binding domain selected from: a migratory locust RXR, a mouse RXR, a honey bee RXR, a beetle RXR, a whitefly RXR, or a leaf hopper RXR. In some embodiments, the ligand binding domain of the RXR is not from human RXR. In some embodiments, the ligand binding domain of the RXR is from a migratory locust RXR.

In some embodiments of the presently-disclosed subject matter, the transactivation domain of the second polypeptide encoded by the modified RXR gene expression cassette is selected from: a VP16 activation domain; a GAL4 activation domain, a p53 activation domain, and a p65 subunit of Nf-kb activation domain. In some embodiments, the transactivation domain is a VP16 activation domain.

In some embodiments of the system, the EcR gene expression cassette and the RXR gene expression cassette are under the control of constitutive promoters. In some embodiments, the constitutive promoters are selected from the group consisting of: 35S promoters; CaMv promoters; and CSV promoters. In some embodiments, the constitutive promoters of the EcR gene expression cassette and the RXR gene expression cassette are 35S promoters.

In some embodiments of the system, the gene-of-interest expression cassette further includes a translational optimization sequence. In some embodiments, the translational optimization sequence comprises the sequence AACAATGGA.

In some embodiments of the system, the promoter of the gene-of-interest expression cassette is selected from: −46 35S promoter; or TATAA promoter. In some embodiments, the promoter of the gene-of-interest expression cassette is −46 35S promoter.

In some embodiments of the system, the ligand is selected from: a diacylhydrazine compound, methoxyfenozide, tubefenozide, halo fenozide, and chromogenozide. In some embodiments, the ligand is methoxyfenozide. In some embodiments, the concentration of ligand for expressing the gene-of-interest is about 15 nM to about 100 nM.

The presently-disclosed subject matter further includes a method of modulating expression of a gene-of-interest in a host plant cell. In some embodiments, the method includes introducing into the host plant cell a system for modulating expression of the gene-of-interest, and introducing into the host plant cell a ligand that binds the ligand-binding domain of the first polypeptide. The system for modulating expression of the gene of interest can include an EcR gene expression cassette for expressing a first polypeptide, including a binding domain that recognizes a response element associated with the gene-of-interest, and a ligand binding domain from an EcR; and an RXR gene expression cassette for expressing a second polypeptide, including (i) a transactivation domain, and a ligand binding domain of a modified RXR, comprising a polypeptide sequence of SEQ ID NO: 1 with at least one amino acid mutation; and a gene-of-interest expression cassette, including the response element to which the binding domain binds, a promoter that is activated by the transactivation domain, and the gene of interest.

In some embodiments of the method, the modified RXR of the ligand binding domain of the second polypeptide includes at least one amino acid mutation is selected from the group consisting of: S122A; A105S; T94A; T81H; A62S; A62S:T81H; and A62S:T81H:V123I.

In some embodiments of the method, the gene-of-interest expression cassette of the system further includes a translational optimization sequence. In some embodiments, the translational optimization sequence comprises the sequence AACAATGGA.

The presently-disclosed subject matter further includes certain isolated nucleic acid molecules and isolated polypeptides. In some embodiments, an isolated nucleic acid comprising a sequence that encodes a polypeptide comprising SEQ ID NO: 1 with at least one amino acid mutation is provided. In some embodiments, an isolated polypeptide comprising SEQ ID NO: 1 with at least one amino acid mutation is provided. In some embodiments, the at least one amino acid mutation is selected from the group consisting of: S122A; A105S; T94A; T81H; A62S; A62S:T81H; and A62S:T81H:V123I.

BRIEF DESCRIPTION OF THE DRAWINGS

FIG. 5A includes the control, FIG. 5B includes the optimization sequence AACAATGGA, FIG. 5C includes the optimization sequence of AAAAATGGA, and FIG. 5D includes the optimization sequence of AACCATGGA.

BRIEF DESCRIPTION OF THE SEQUENCE LISTING

Figure 1:
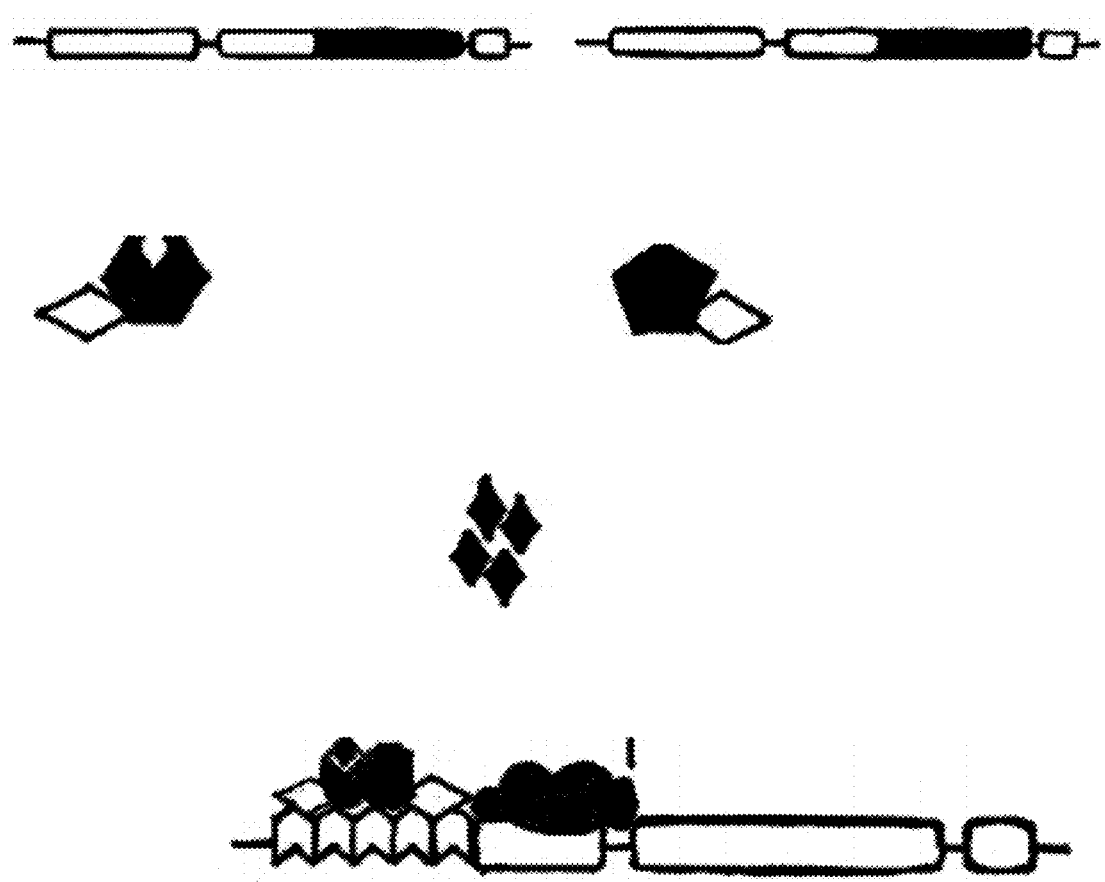
FIG. 1 is a schematic representation of a gene expression modulation system for use in plants.

SEQ ID NO: 1 is an amino acid sequence from LmRXR.

SEQ ID NO: 2 is a forward primer used to make a S122A modification to the amino acid of SEQ ID NO: 1 in the studies described in the Examples.

SEQ ID NO: 3 is a reverse primer used to make a S122A modification to the amino acid of SEQ ID NO: 1 in the studies described in the Examples.

SEQ ID NO: 4 is a forward primer used to make an A105S modification to the amino acid of SEQ ID NO: 1 in the studies described in the Examples.

SEQ ID NO: 5 is a reverse primer used to make an A105S modification to the amino acid of SEQ ID NO: 1 in the studies described in the Examples.

SEQ ID NO: 6 is a forward primer used to make a T94A modification to the amino acid of SEQ ID NO: 1 in the studies described in the Examples.

SEQ ID NO: 7 is a reverse primer used to make a T94A modification to the amino acid of SEQ ID NO: 1 in the studies described in the Examples.

SEQ ID NO: 8 is a forward primer used to make a T81H modification to the amino acid of SEQ ID NO: 1 in the studies described in the Examples.

SEQ ID NO: 9 is a reverse primer used to make a T81H modification to the amino acid of SEQ ID NO: 1 in the studies described in the Examples.

SEQ ID NO: 10 is a forward primer used to make an A62S modification to the amino acid of SEQ ID NO: 1 in the studies described in the Examples.

SEQ ID NO: 11 is a reverse primer used to make an A62S modification to the amino acid of SEQ ID NO: 1 in the studies described in the Examples.

SEQ ID NO: 12 is a forward primer used to make a V123I modification to the amino acid of SEQ ID NO: 1 in the studies described in the Examples.

SEQ ID NO: 13 is a reverse primer used to make a V123I modification to the amino acid of SEQ ID NO: 1 in the studies described in the Examples.

SEQ ID NO: 14 is a forward primer used to verify the integration of the AAAAATGGA sequence in the studies described in the Examples.

SEQ ID NO: 15 is a forward primer used to verify the integration of the AACCATGGA sequence in the studies described in the Examples.

SEQ ID NO: 16 is a forward primer used to verify the integration of the AACAATGG sequence in the studies described in the Examples.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK® accession numbers. The sequences cross-referenced in the GENBANK® database are expressly incorporated by reference as are equivalent and related sequences present in GENBANK® or other public databases. Also expressly incorporated herein by reference are all annotations present in the GENBANK® database associated with the sequences disclosed herein. Unless otherwise indicated or apparent, the references to the GENBANK® database are references to the most recent version of the database as of the filing date of this Application.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

The presently-disclosed subject matter includes systems and methods for modulating expression of a gene-of-interest in a host plant cell.

As used herein, the term "modulate" refers to any change in expression of a gene of interest, including an increase or decrease in expression of a gene-of-interest. As such, modulation of a gene-of-interest can include over-expressing, under-expressing, or substantially blocking expression of the gene-of-interest in a host plant cell.

The term "gene" is used broadly to refer to any segment of DNA associated with a biological function. Thus, genes include, but are not limited to, coding sequences and/or the regulatory sequences required for their expression. Genes can also include non-expressed DNA segments that, for example, form recognition sequences for a polypeptide. Genes can be obtained from a variety of sources, including cloning from a source of interest or synthesizing from known or predicted sequence information, and can include sequences designed to have desired parameters. Examples of genes that can be modulated in accordance with the presently-disclosed subject matter include, but are not limited to, the following: insecticidal genes, such as Bt and protease inhibitors; anti-bacterial and anti-fungal genes, such as defensin; genes toxic to or which inhibit development of insects, pathogens, and nematodes; and the like.

As used herein, the term "plant cell" is understood to mean any cell derived from a monocotyledonous or a dicotyledonous plant. The term "plant" is understood to mean any differentiated multicellular organism capable of photosyntheis, including monocotyledons and dicotyledons, with specific examples including, but not limited to: Arabidopsis, tobacco, corn, or soybean.

The EcR-based system for modulating expression of a gene-of-interest (or gene switch) as described herein has a two-hybrid format and uses a modified retinoid x receptor (RXR) as a partner. The EcR-RXR gene switch has little or no basal expression in the absence of a ligand, works with a wide range of concentrations, including nM concentrations of ligand, and works in a variety of plant species. Additionally, the EcR-RXR gene switch works with ligands that are already registered for field use and are easily applied, making the gene switch useful for large-scale field applications.

In some embodiments of the presently-disclosed subject matter, the system includes an EcR gene expression cassette, an RXR gene expression cassette, and a gene-of-interest expression cassette, each of which are capable of being expressed in a host plant cell.

The term "expression cassette" refers to a nucleic acid molecule capable of directing expression of a particular nucleotide sequence in an appropriate host cell, comprising a promoter operatively linked to the nucleotide sequence of interest which is operatively linked to termination signals. It can also include sequences required for proper translation of the nucleotide sequence. The coding region usually encodes a polypeptide of interest but can also encode a functional RNA of interest, for example antisense RNA or a non-translated RNA, in the sense or antisense direction. The expression cassette comprising the nucleotide sequence of interest can be chimeric, meaning that at least one of its components is heterologous with respect to at least one of its other components. The expression cassette can also be one that is naturally occurring but has been obtained in a recombinant form useful for heterologous expression.

Typically, however, the expression cassette is heterologous with respect to the host; i.e., the particular DNA sequence of the expression cassette does not occur naturally in the host cell and was introduced into the host cell or an ancestor of the host cell by a transformation event. The expression of the nucleotide sequence in the expression cassette can be under the control of a constitutive promoter or of an inducible promoter that initiates transcription only when the host cell is exposed to some particular external stimulus. In the case of a multicellular organism such as a plant, the promoter can also be specific to a particular tissue, organ, or stage of development.

The EcR gene expression cassette of the presently-disclosed subject matter includes a nucleotide sequence that encodes a first polypeptide, while the RXR gene expression cassette includes a nucleotide sequence that encodes a second polypeptide.

The terms "nucleotide" and "nucleic acid" refers to deoxyribonucleotides or ribonucleotides and polymers thereof in either single or double stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed base and/or deoxyinosine residues (Batzer et al. (1991) Nucleic Acid Res 19:5081; Ohtsuka et al. (1985) J Biol Chem 260:2605 2608; Rossolini et al. (1994) Mol Cell Probes 8:91 98).

As used herein, the term "polypeptide" means any polymer comprising any of the 20 protein amino acids, regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The term further encompasses fusion proteins. As used herein, the terms "protein", "polypeptide," and "peptide" are used interchangeably when referring to a gene product or amino acid produced using an expression cassette.

The gene-of-interest expression cassette includes a response element and a promoter. The first polypeptide encoded by the EcR expression cassette includes a DNA-binding domain that recognizes the response element of the gene-of-interest expression cassette. The first polypeptide also includes a ligand binding domain, which is capable of receiving a ligand. The second polypeptide includes a modified RXR ligand binding domain and a transactivation domain capable of activating the promoter of the gene-of-interest expression cassette. The first polypeptide and the second polypeptide dimerize in the presence of the ligand. The DNA-binding domain binds the response element of the gene-of-interest expression cassette, while the transactivation domain activates the promoter of the gene-of-interest expression cassette. In this manner, when the first and second polypeptides dimerize in the presence of the ligand expression of the gene-of-interest is affected.

With reference to FIG. 1, in some embodiments of the presently-disclosed subject matter, a system 10 for modulating expression of a gene-of-interest 30 in a host plant cell includes: an EcR gene expression cassette 12, and an RXR gene expression cassette 14, both of which are capable of being expressed in a host plant cell and both of which are under the control of constitutive promoters 16, 18. The system 10 also includes a gene-of-interest expression cassette 20 for expressing the gene-of-interest 30 in the host plant cell.

The EcR gene expression cassette 12 includes a first polynucleotide encoding a first polypeptide 22, which includes a ligand-binding domain 24 and a DNA-binding domain 26, for recognizing a response element 28 of the gene-of-interest expression cassette 20. The ligand-binding domain 24 of the first polypeptide 22 can include an ecdysone receptor ligand binding domain.

The EcR ligand binding domain have the sequence of a wild type *Choristoneura furniferana* (spruce budworm) EcR (CfEcR) ligand binding domain or another EcR ligand binding domain selected from the group including, but not limited to: a moth EcR, a butterfly EcR, a fly EcR, a mosquito EcR, a beetle EcR, a locust EcR, a whitefly EcR, a fruit fly EcR, a honey bee EcR, and a leaf hopper EcR.

In some embodiments, the EcR ligand binding domain includes twelve helices. In some embodiments the EcR ligand binding domain is a truncated EcR ligand binding domain. A truncated EcR refers to an EcR that includes fewer residues than a full-length wild type EcR. The term "truncated" when used to refer to a polypeptide refers to an amino acid sequence wherein one or more amino acids have been removed relative to a reference polypeptide. For example, with reference to GENBANK® Accession Number AAC36491 of the full-length 541 amino acid EcR, in some embodiments, a truncated EcR will include at least amino acids 196-541 of the full-length EcR. In some embodiments, a truncated EcR will include at least 350, 375, 400, 425, 450, 475, 500, or 525 amino acids.

The DNA binding domain and the response element should be selected as a pair, such that the DNA binding domain that is selected will recognize the response element that is selected; however, so long as the selected DNA binding domain recognizes the selected response element, any such pair may be selected, i.e., any DNA binding domain with a known response element will work, and conversely, any response element with a known DNA binding domain will work. For example, in some embodiments, the DNA binding domain (DBD) and response element (RE) are selected from: GAL4 147 DBD and RE; GAL4 65 DBD and RE; GAL4 93 DBD and RE; LexA DBD and RE; Lac repressor DBD and RE.

In some embodiments, the EcR gene expression cassette is under the control of a constitutive promoter. In some embodiments, the constitutive promoter is selected from the group consisting of a 35S promoter, a CaMv promoter, and a CSV promoter. In some embodiments, the constitutive promoter is a 35S promoter.

With continued reference to FIG. 1, the RXR gene expression cassette 14 encodes a second polypeptide 32 having a transactivation domain 34. The transactivation domain used for the gene switch can also be selected from a variety of alternative transactivation domains, so long as the selected transactivation domain is capable of activating the promoter being used in the gene-of-interest expression cassette. Examples of transactivation domains that can be used include, but are not limited to, the following: a VP16 activation domain; a truncated or minimal VP16 transactivation domain containing core activation domain residues (single or multiple copies); a GAL4 transactivation domain; p53 transactivation domains; p65 Subunit of NF-kb activation domain; and the like.

The second polypeptide 32 expressed by the RXR gene expression cassette 14 further includes a ligand binding domain of a modified RXR 42. The term "modified" when used to refer to a polypeptide refers to an amino acid sequence that is different from a reference polypeptide by one or more amino acids, e.g., one or more amino acid substitutions or mutations. The modified RXR 42 can comprise a polypeptide sequence of SEQ ID NO: 1 that has been modified with at least one amino acid mutation. SEQ ID NO: 1 has the amino acid sequence of a 1-8 helices region of RXR from wild type *Locusta migratoria* (LHTDM PVERI LEAEK RVECK AENQV EYELV EWAKH IPHFT SLPLE DQVLL LRAGW NELLI AAFSH RSVDV KDGIV LATGL TVHRN SAHQA GVGTI FDRVL TELVA KMREM KMDKT ELGCL RSVIL FNPE).

In some embodiments, the modified RXR ligand binding domain can include the amino acid sequence of 1-12 helices of an RXR, including at least one amino acid mutation in the portion of the RXR ligand binding domain corresponding to the 1-8 helices region, e.g., SEQ ID NO: 1. In some embodiments, the modified RXR ligand binding domain is a truncated modified RXR ligand binding domain. For example, with reference to GENBANK® Accession Number AAQ55293 for wild type LmRXR, a modified RXR ligand binding domain can include the wild type amino acid sequence with one or more amino acid mutations, and a truncated RXR ligand binding domain can include the wild type amino acid sequence with one or more amino acids deletions.

Examples of amino acid mutations in the portion of the RXR ligand binding domain corresponding to SEQ ID NO: 1 include, but are not limited to, the following: S122A; A105S; T94A; T81H; A62S; A62S:T81H; and A62S:T81H:V123I.

Although the portion of the RXR corresponding to the 1-8 helices region of RXR will often have the sequence of SEQ ID NO: 1 with at least one amino acid mutation, remaining portions of the RXR (e.g., 9-12 helices region) can have the sequence of an RXR that is selected from: a migratory locust RXR, a mouse RXR, a honey bee RXR, a beetle RXR, a whitefly RXR, or a leaf hopper RXR. In some embodiments, the RXR is not a human RXR. In some embodiments, the RXR is from a migratory locust (Locusta migratoria) RXR (LmRXR).

In some embodiments, the modified RXR gene expression cassette is under the control of a constitutive promoter. In some embodiments, the constitutive promoter is selected from the group consisting of a 35S promoter, a CaMv promoter, and a CSV promoter. In some embodiments, the constitutive promoter is a 35S promoter.

With continued reference to FIG. 1, in the presence of a ligand 36 recognized by the ligand-binding domain 24 of the first polypeptide 22, the first polypeptide 22 and the second polypeptide 32 dimerize 38. The DNA-binding domain 26 binds the response element 28 of the gene-of-interest expression cassette 20. The gene-of-interest expression cassette 20 also includes a promoter 40 that is activated by the transactivation domain 34. As such, when the polypeptides 22, 32 dimerize 38, the DNA-binding domain 26 binds the response element 28 and the transactivation domain 34 activates the promoter 40 of the gene-of-interest expression cassette 20, thereby affecting expression of the gene-of-interest.

Examples of ligands that can be used with the system include any ligand capable of binding the ligand binding domain and affecting modulation of the gene-of-interest in the system of the present invention, including methoxyfenozide, tubefenozide, halo fenozide, chromofenozide, diacylhydrazine compounds, and the like.

In some embodiments, the gene-of-interest expression cassette 20 of the system 10 further includes a translational optimization sequence 44. The translational optimization sequence 44 can be placed between the promoter 40 and the gene-of-interest 30. The translational optimization sequence 44 can include coding and non-coding portions, such that, in some embodiments, the polypeptide product of the gene-of-interest 30 can include amino acid residues coded by the translational optimization sequence 44 portion of the gene-of-interest expression cassette 20. For example, in some embodiments the translational optimization sequence 44 can be AACAATGGA, wherein the first amino acid residues of the polypeptide product of the gene-of-interest 30 is methionine (coded by ATG, amino acids 5-7 of the translational optimization sequence).

The system of the presently-disclosed subject matter can be used to practice a method of modulating the expression of a gene-of-interest in plants. The ability to so modulate expression of a gene-of-interest in plants is useful, for example, to investigate gene function or to select predetermined plants in an agricultural setting without the use of herbicides and/or pesticides. Any gene whose function is desired to be investigated or of which the expression is desired to be modulated may be selected for expression modulation in accordance with the method of the presently-disclosed subject matter.

As such, the presently-disclosed subject matter further includes a method of modulating expression of a gene-of-interest in a host plant cell. In some embodiments, the method includes introducing into the host plant cell an EcR gene expression cassette for expressing a first polypeptide as described herein above, an RXR gene expression cassette for expressing a second polypeptide as described herein above, and a gene-of-interest expression cassette as described herein above; and introducing into the host plant cell a ligand that binds a ligand-binding domain of the first polypeptide; wherein the first polypeptide and the second polypeptide dimerize in the presence of the ligand and affect expression of the gene-of-interest. The expression cassettes may be introduced into plant host cells by methods known to those skilled in the art.

The presently-disclosed subject matter further includes an isolated nucleic acid and an isolated polypeptide. The term "isolated", when used in the context of an isolated nucleic acid molecule or an isolated polypeptide, is a nucleotide or polypeptide that, by the hand of man, exists apart from its native environment and is therefore not a product of nature. An isolated nucleic acid molecule or polypeptide can exist in a purified form or can exist in a non-native environment such as, for example, in a transgenic host cell.

In some embodiments, the presently-disclosed subject matter includes an isolated nucleic acid comprising a sequence that encodes a polypeptide comprising SEQ ID NO: 1 with at least one amino acid mutation. In some embodiments, the at least one amino acid mutation is selected from the group consisting of: S122A; A105S; T94A; T81H; A62S; A62S:T81H; and A62S:T81H:V123I.

In some embodiments, the presently-disclosed subject matter includes an isolated polypeptide comprising SEQ ID NO: 1 with at least one amino acid mutation. In some embodiments, the at least one amino acid mutation is selected from the group consisting of: S122A; A105S; T94A; T81H; A62S; A62S:T81H; and A62S:T81H:V123I.

The presently-disclosed subject matter is further illustrated by the following specific but non-limiting examples. The following examples may include compilations of data that are representative of data gathered at various times during the course of development and experimentation related to the present invention.

EXAMPLES

Chemically inducible gene regulation systems have applications for the precise regulation of transgene expression in plants and animals. Recent advancement in a two hybrid ecdysone receptor (EcR) based gene switch in host animal cells was achieved using a chimera, identified as chimera 9(CH9), between *Homo sapiens* retinoid x receptor (HsRXR) and insect, *Locusta migratoria* RXR (LmRXR) as partner with *Choristoneura fumiferana* EcR (CfEcR) in inducing expression of the luciferase reporter gene (Tavva et al. 2007). The two hybrid gene switch containing chimera 9 (CH9) along with CfEcR was useful in terms of low-background activity in the absence of ligand and high induced expression levels of the reporter gene in the presence of ligand. An attempt for host plant cell use of the gene switch including chimera 9, which involved the use of human RXR and LmRXR, would have at least bio-safety and social acceptance issues. These examples include descriptions of studies related to embodiments of the presently-disclosed gene switches that have benefits comparable to, without certain drawbacks associated with, the CH9-containing gene switch.

Each of the exemplary embodiments of the gene switch described in these examples is a two hybrid EcR gene switch containing LmRXR as its partner, where there is at least one amino acid mutation in the amino acids residues of the 1-8 helices of LmRXR. The amino acid sequence of the 1-8 helices of LmRXR is identified as SEQ ID NO: 1. The exemplary embodiments also include a translational optimization polynucleotide sequence upstream of the coding rejoin of the gene whose expression is modulated. The following sequences were tested for use as a translational optimization polynucleotide sequence: AACAATGGA, AAAAATGGA, and AACCATGGA. As shown in these examples, the exemplary embodiments of the gene switch has very low background expression in the host plant cells in the absence of ligand, and high induction of luciferase reporter in the host plant cells at low concentrations of ligand, e.g., as low as about 16-80 nM concentrations.

Materials and Methods

Various LmRXR mutants were generated by changing amino acids residues in 1-8 helices by site-directed mutagenesis. The following mutants were generated: S122A (Lm1); A105S (Lm2); T94A (Lm3); T81H (Lm4); A62S (Lm5); A62S:T81H (Lm6); A62S:T81H:V123I (Lm7). These mutants are collectively referred to in these examples as the LmRXR mutants.

Site-directed mutagenesis was carried out by using the quick change site-directed mutagenesis kit (Stratagene). Mutations were verified by sequencing. Several sets of primers were used to change the amino acids residues in 1-8 helices of LmRXR corresponding to HsRXR. These primers included:

LmS122A (F) 5'-CTT GGC TGC TTG CGA GCT GTT ATT CTT TTC AAT CC-3' (SEQ ID NO: 2)
LmS122A (R) 5' GGA TTG AAA AGA ATA ACA GCT CGC AAG CAG CCA AG-3' (SEQ ID NO: 3)
LmA105S (F) 5' TTG ACA GAA CTG GTA TCA AAG AT GAGA GAA ATG-3'(SEQ ID NO: 4)
LmA105S (R) 5' CAT TTC TCT CAT CTT TGA TAC CAG TTC TGT CAA-3' (SEQ ID NO: 5)
LmT94A (F) 5' CAA GCT GGA GTC GGC GCA ATA TTT GAC AGA GTT TTG-3' (SEQ ID NO: 6)
LmT94A (R) 5' CAA AAC TCT GTC AAA TAT TGC GCC GAC TCC AGC TTG-3' (SEQ ID NO: 7)
LmT81H (F) 5' CTT GCC ACT GGT CTC CAC GTG CAT CGA AAT TCT GCC-3' (SEQ ID NO: 8)
LmT81H (R) 5' GGC AGA ATT TCG ATG CAC GTG GAG ACC AGT GGC AA-3' (SEQ ID NO: 9)
LmA62S (F) 5' GAA CTG CTA ATT GCA TCA TTT TCA CAT CGA TCT G-3' (SEQ ID NO: 10)
Lm A62S (R) 5' CAG ATC GAT GTG AAA ATG ATG CAA TTA GCA GTT C-3' (SEQ ID NO: 11)
Lm V123I (F) 5' TGG CTG CTT GCG ATC TAT TAT TCT TTT CAA TCC-3' (SEQ ID NO: 12)
Lm V123I (R) 5' GGA TTG AAA AGA ATA GAT CGC AAG CAG CCA-3' (SEQ ID NO: 13)

For transient expression studies, the LmRXR mutants receptor and reporter (−46 35S:Luc/−46 35S:KLuc/−31 35S: KLuc) gene expression cassettes were cloned into the pKYLX80 vector. The LmRXR mutants were cloned downstream of the VP16 AD sequence in pVP16 vector (BD Biosciences Clonetech, San Jose, Calif., U.S.A). DNA sequences coding for the fusion proteins of VP16 AD and RXR mutants were transferred from pVP16RXR mutant constructs using NheI and XbaI restriction endonucleases and cloned into the XbaI restricted pKYLX80 vector. The resulting constructs were designated pK80Lm-1-pK80Lm-7. A detailed description of the construction of pK80GCfE was described in detail by Tavva et al. (2006).

Kozak sequences were placed upstream to the luciferase reporter gene and screened for better transgene expression in plants. For the reporter expression cassette, −46 and −31 35S minimal promoters were cloned into pKYLX80 vector as described by Tavva et al. (2006). The luciferase reporter gene was PCR-amplified from the pFRLuc vector (Stratagene, La Jolla, Calif., USA) using several sets of primers having different Kozak sequence and cloned into pGEM-T Easy vector to verify the integration of Kozak sequences sequence. These primers included:

KZKLUC2 (F): 5'-CTC GAG AAA AAT GGA AGA CGC CAA AAA CAT AAA G-3' (SEQ ID NO: 14)
KZKLUC4 (F): 5'-CTC GAG AAC CAT GGA AGA CGC CAA AAA CAT AAA G-3' (SEQ ID NO: 15)
KZKLUC1 (F): 5'-CTC GAG AAC AAT GGA AGA CGC CAA AAA CAT AAA G-3' (SEQ ID NO: 16)

The luciferase reporter gene with Kozak sequence was then excised from the pGEM-T Easy vector and cloned into XhoI/SacI sites downstream of the minimal −46 35S minimal promoter in the modified pKYLX80 vector. The reporter gene expression cassette with the pKYLX80 background was designated as pK80-46 35S:KLuc. The full-length luciferase gene was cloned into the pKYLX80 vector under the control of the CaMV 35S$^2$ promoter and used as a positive control in transient expression studies.

Figure 2:
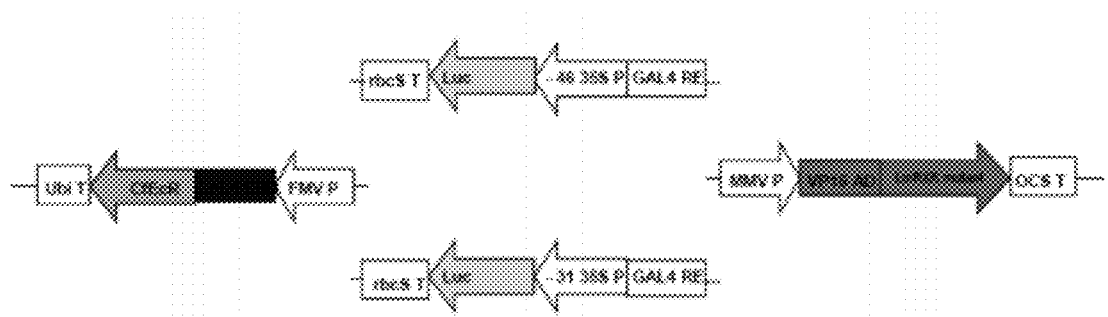
FIG. 2 includes schematic representations of binary vectors with different minimal promoters. p2300:Lm7:KLuc:T-DNA region of the pCAMBIA2300 binary vector showing the assembly of receptor and reporter expression cassettes. $35S^2$ P CaMV 35S promoter with double enhancer sequence, T rbcs Poly A sequence, FMV P figwort mosaic virus promoter, Ubi T ubiquitin 3 terminator, MMV P *Mirabilis* mosaic virus promoter OCS T *Agrobacterium tumefaciens* octopine synthase poly A.
Figure 3A:
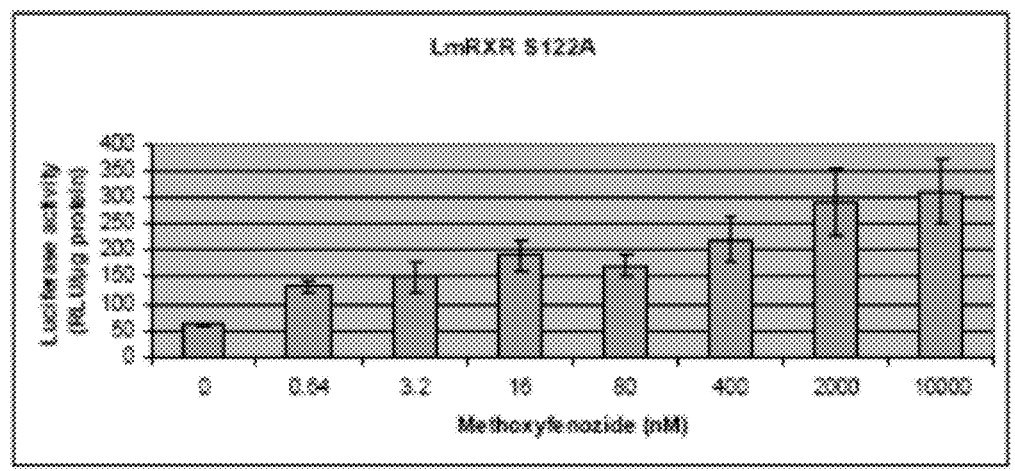
FIGS. 3A-3F are a series of bar graphs showing the results of a screening of different LmRXR mutants in transient expression studies using tobacco protoplasts, including S122A (Lm-1) (FIG. 3A), A105S (Lm-2) (FIG. 3B), T94A (Lm-3) (FIG. 3C), T81H (Lm-4) (FIG. 3D), A62S (Lm-5) (FIG. 3E), and control (wild type) (FIG. 3F). In order to determine the dose-dependent induction of the luciferase gene by EcR gene switches. Tobacco protoplasts were electroporated with pK80GCfE+pK80Lm mutants (Lm-1-Lm-5) and reporter construct. Electroporated protoplasts were exposed to varying concentrations of methoxyfenozide. Luciferase activity was measured after 24 h of incubation and the values were expressed as relative light units per microgram protein.
Figure 3B:
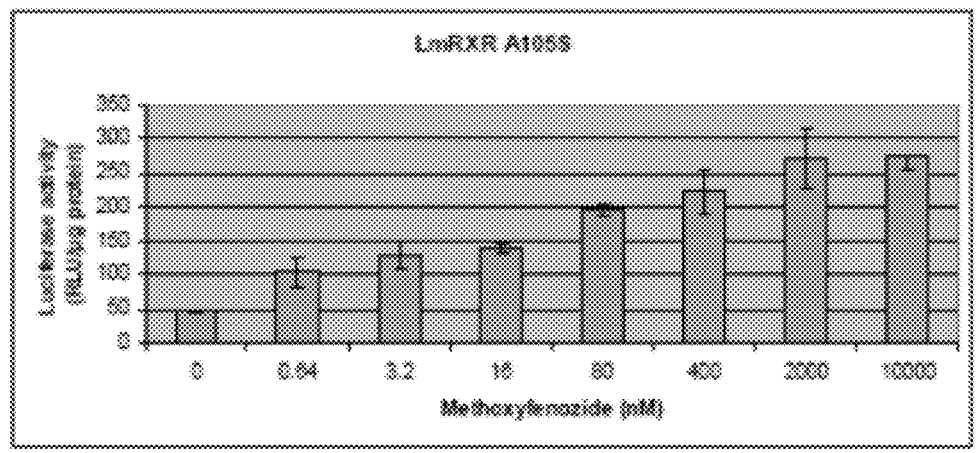
Figure 3C:
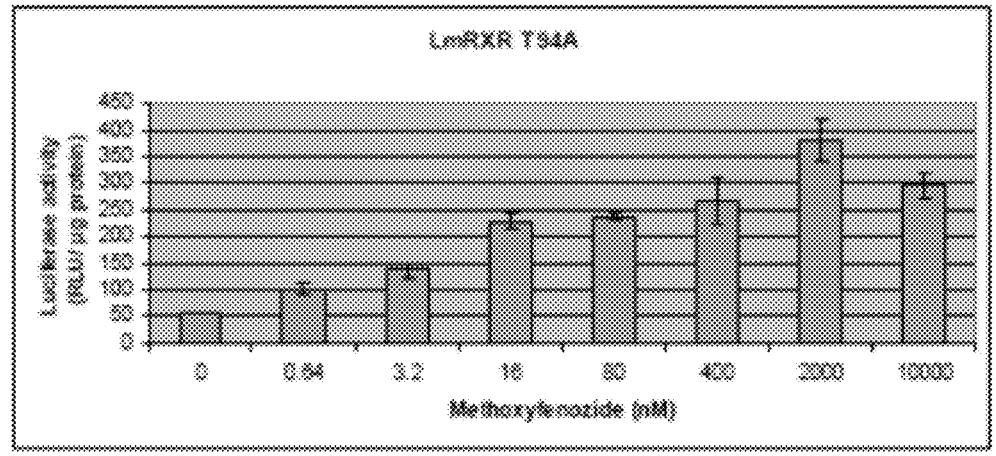
Figure 3D:
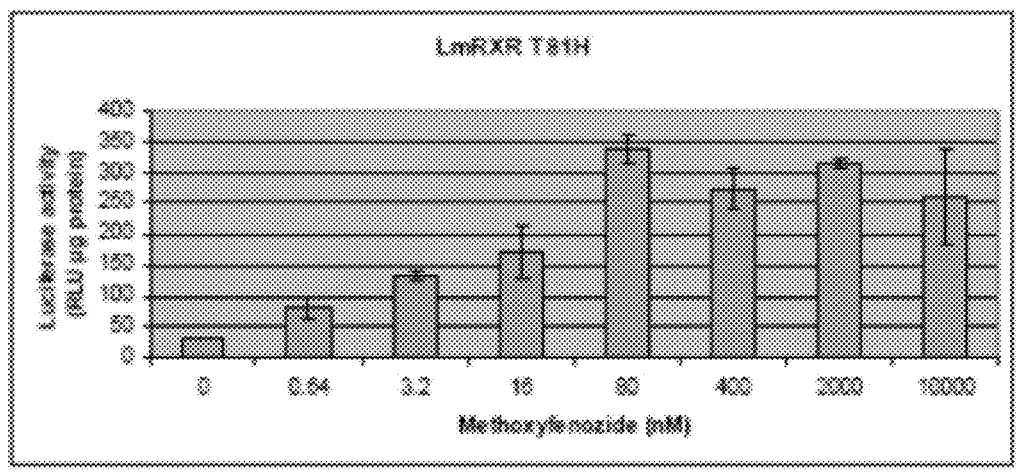
Figure 3E:
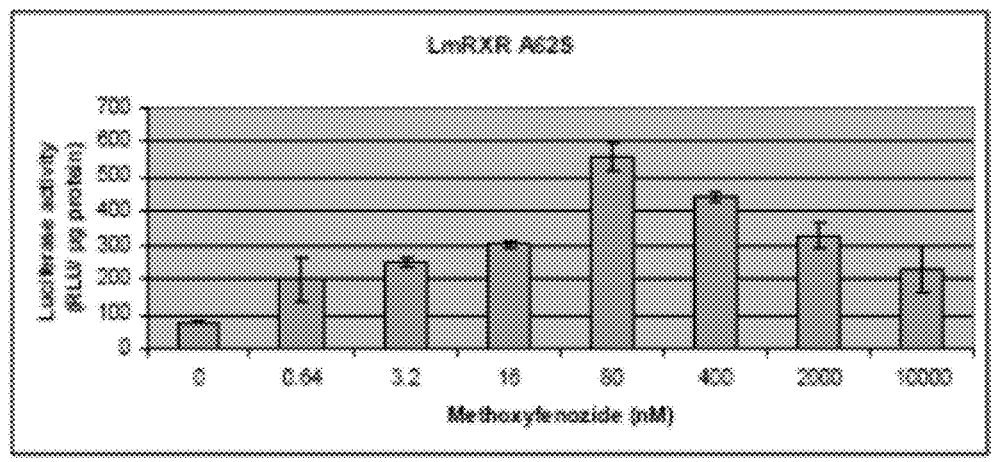
Figure 3F:
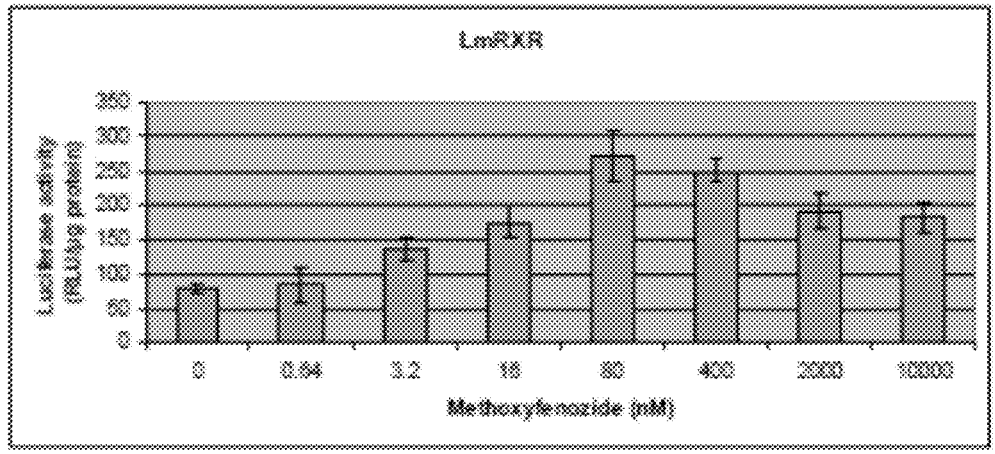

Binary vectors for stable transformation of *Arabidopsis thaliana* were constructed in pCAMBIA2300 vectors (CAMBIA, Can berra, Australia). To construct the binary vector for plant transformation, the GAL4 DBD:CfEcR fusion gene was cloned under the figwort mosaic virus (FMV) promoter and Ubiquitin 2 (Ubi) terminator sequence and the VP16 AD: mutant Lm-1-Lm-7 fusion gene were cloned under the mirabilis mosaic virus (MMV) promoter and *Agrobacterium tumefaciens* octopine synthase (Ocs) poly A sequence. The FMV- and MMV-driven expression cassettes were assembled into pSL301 vector. The reporter and receptor expression cassettes were excised with appropriate restriction enzymes and assembled into the pCAMBIA2300 vector for plant transformation. The resulting binary vector was designated as p2300:Lm7:luc (FIG. 2).

Transient expression studies—Transient expression studies were carried out by isolating protoplasts from cell suspension cultures of tobacco (*Nicotiana tabacum* cv. Xanthi-Brad). A detailed description of the isolation and electroporation of protoplasts was described earlier by Tavva et al. (2006).

Dose response study with tobacco protoplasts—Methoxyfenozide dose-dependent performance of different LmRXR mutants (Lm-1-Lm-7) in inducing luciferase reporter gene activity in a two-hybrid gene switch was tested by co-electroporating pK80-46 35S:KLuc, pK80GCfE, and mutant LmRXR (pK80VLm1-Lm7) constructs. The electroporated protoplasts were incubated in the growth medium containing 0, 0.64, 3.2, 16, 80, 400, 2000, 10 000 nM concentrations of methoxyfenozide. After 24 h of addition of ligand, the protoplasts were assayed for luciferase reporter gene activity using a Fluoroscan FL plate reader (Fluoroscan Ascent FL, Thermo biosystems Milford, Mass., U.S.A) as described earlier (Tavva et al. 2006).

Plant tissue culture—*Arabidopsis thaliana* (L.) Heynth. ecotype Columbia ER was used for plant transformation experiments. The binary vector (p2300 CfEcR:LmRXR mutant (Lm-1-Lm-7): Luc) constructs for plant transformation was mobilized into *Agrobacterium tumefaciens*, strain GV3850 by freeze-thaw method. *Arabidopsis* plants were transformed using the whole plant-dip method (Clough and Bent 1998). Transgenic *Arabidopsis* plants were selected by germinating the seeds collected from the infiltrated plants on medium containing 50 mg/l kanamycin. The analysis of transgenic plants for luciferase induction level was carried out on T2 seeds plated on kanamycin containing medium.

Dose response study with T2 *Arabidopsis* plants—Seeds collected from four T2 *Arabidopsis* lines were plated on agar media containing 50 mg/l kanamycin and different concentrations of methoxyfenozide (0, 0.64, 3.2, 16, 80, 400, 2000, 10 000 nM). The seeds were allowed to germinate and grew on the induced media for 20 days at 25° C., 16 h light/8-h dark. Three seedlings from each plate were collected separately and ground in a volume of 100 µl of 1× passive lyses buffer (Promega corporation, Madison, Wis., USA) and luciferase activity was measured.

Soil Applications of Methoxyfenozide

Time-course and study with soil-grown plants—T2 *Arabidopsis* plants were transferred to a greenhouse in a time-course study involving the application of 0, 0.64, 3.2, 16, 80, 400, 2000, 10 000 nM methoxyfenozide to the soil. Care was taken not to leach out any excess solution. Leaf discs were collected at 0, 1, 2, and 4 days after application of methoxyfenozide and luciferase activity in each leaf disk was measured.

Dose-response study with soil grown plants—T2 *Arabidopsis* plants were transferred to the greenhouse for a dose response experiment. These plants were allowed to grow in the greenhouse until the *Arabidopsis* plants had a complete whorl of rosette leaves. Different doses of methoxyfenozide, 0, 0.64, 3.2, 16, 80, 400, 2000, 10 000 nM were applied to the pots three times at 2 days intervals. Leaf disks were collected on day 4 and luciferase activity was measured in each leaf disk.

Results

Transient Expression Studies with Tobacco Protoplasts

Figure 4:
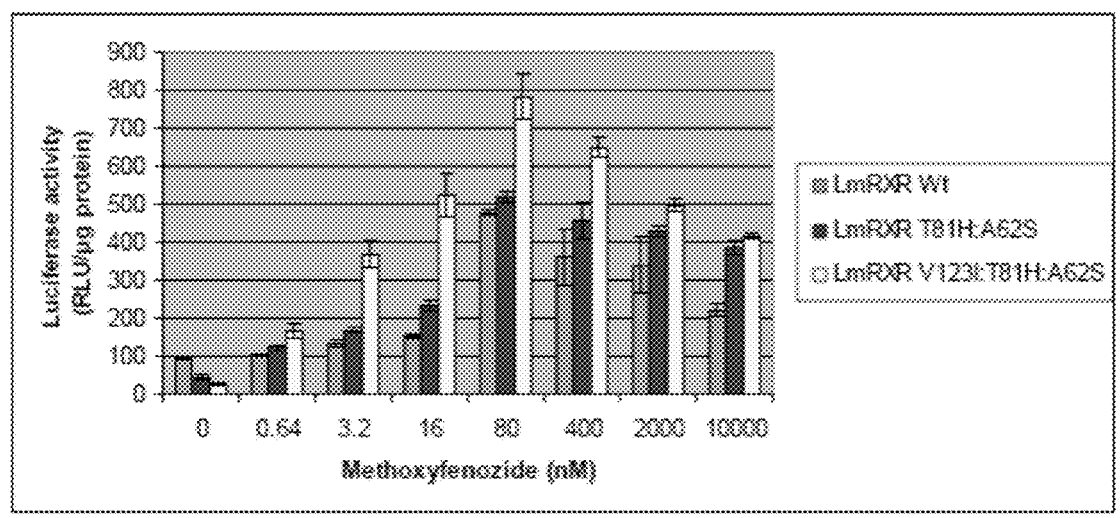
FIG. 4 is a bar graph comparing the dose-dependent induction of the luciferase gene by EcR gene switches containing wild-type LmRXR, LmRXR mutant [Lm-6 (T81H:A62S)], and LmRXR mutant [Lm-7 (T81H:A62S:V123I)].
Figure 5A:
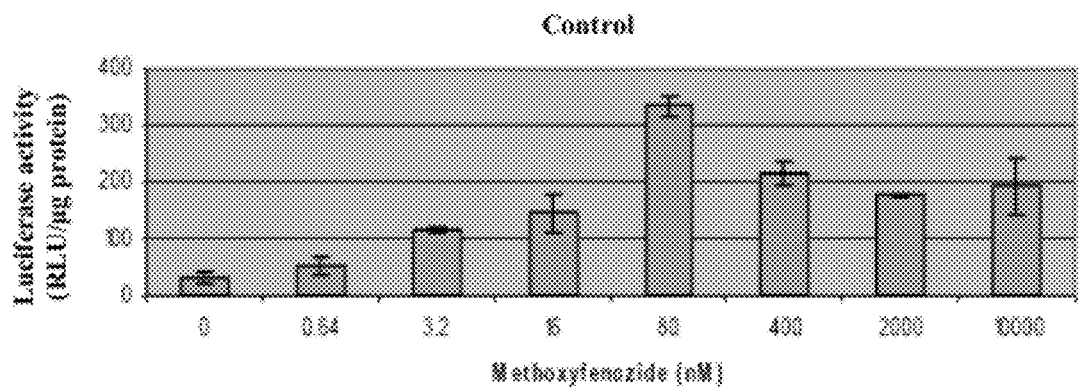
FIGS. 5A-5D are a series of bar graphs showing the dose-dependent induction of the luciferase gene by EcR gene switches involving LmRXR, where different translational optimization sequences were integrated upstream to the coding region of luciferase gene.
Figure 5B:
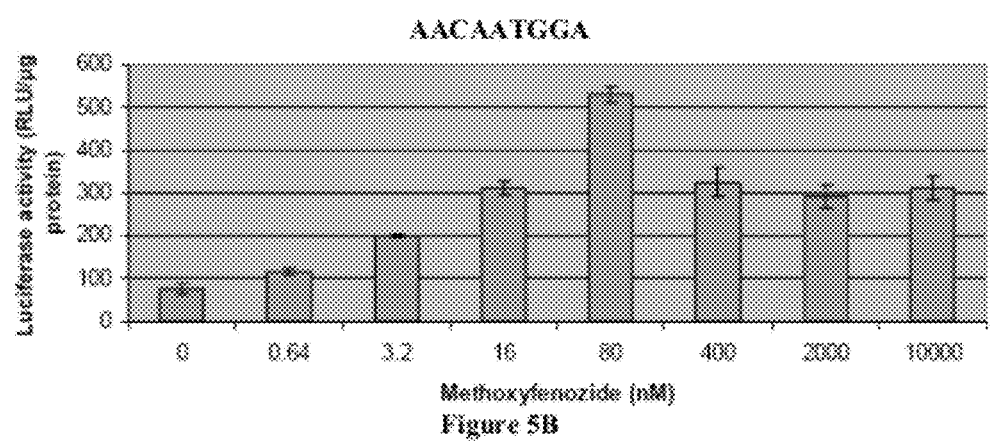
Figure 5C:
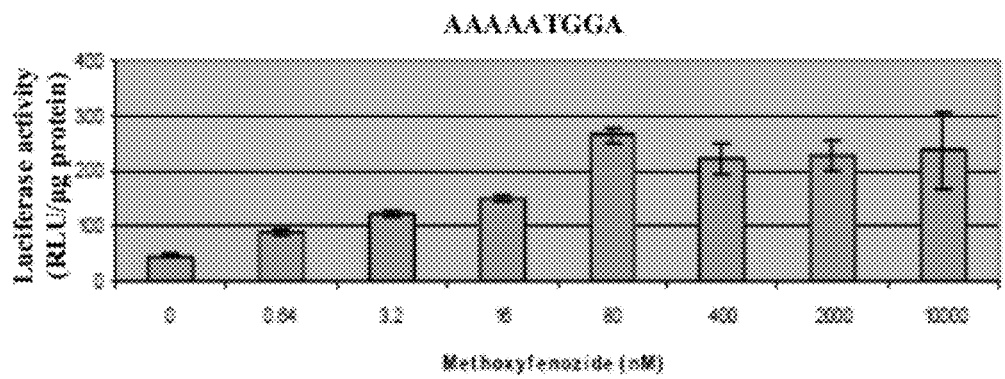
Figure 5D:
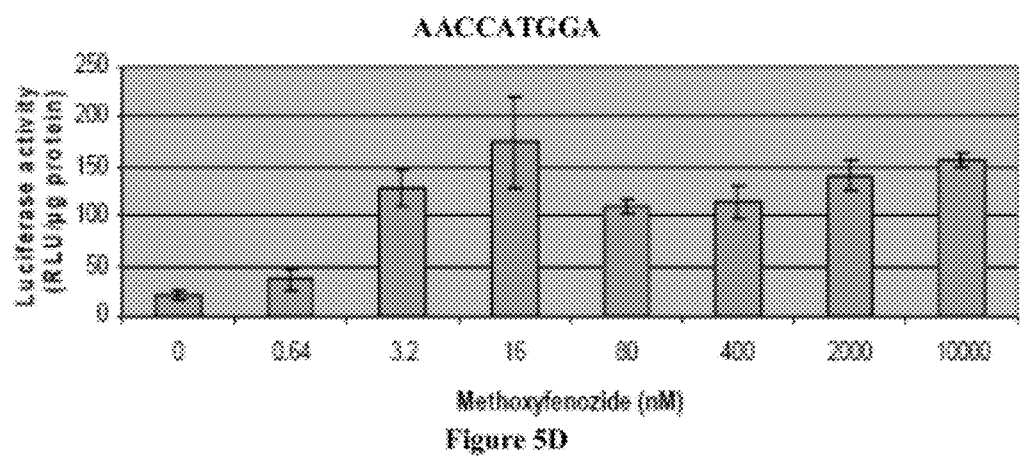

RXR mutagenesis: Site-directed mutagenesis was carried out to change amino acid residues in 1-8 helices of LmRXR (SEQ ID NO: 1). The performance of different RXR mutants (Lm-1-Lm-7) in inducing luciferase reporter gene activity in a two-hybrid format was tested by co-electroporating pK80-46 35S/pK80-46 35S:KLuc, pK80 GCfE and pK80 Lm-1-Lm-7. Among the LmRXR mutants tested in transient expression studies, Lm-4 (LmT81H) mutant showed low background activity in the absence of ligand while Lm-5 (LmA62S) mutant resulted high induction level compared to wild-type LmRXR (FIG. 3). In order to combine the desirable properties of these two LmRXR mutants (Lm-4 and Lm-5), the present inventors incorporated these two mutations together. As desired, LmRXR double mutant Lm-6 (Lm T81H:A62S) showed low background activity in the absence of ligand compared to wild-type LmRXR, but also showed less induction of luciferase. With the aim to increase the induction levels, the present inventors put some more mutations on top of Lm-6 mutant. The present inventors found that Lm-7 (Lm T81H:A62S:V123I) mutant showed low background activity in the absence of ligand and very high induction level compared to wild-type LmRXR and Lm-6 (T81H: A62S) in the presence of 16-80 nM methoxyfenozide (FIG. 4).

Figure 6:
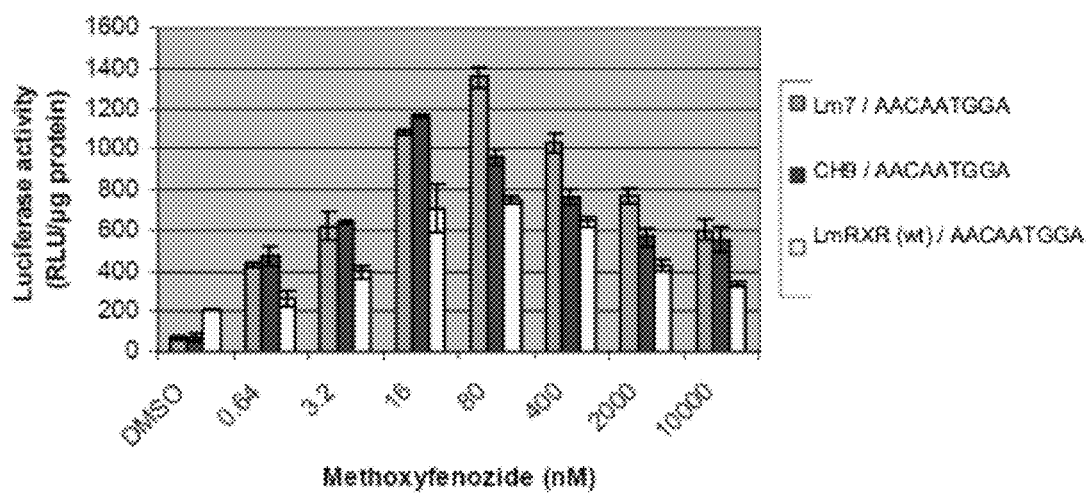
FIG. 6 is a bar graph comparing induction of luciferase in response to different doses of methoxyfenozide by EcR gene switches containing the Lm-7 LmRXR mutant, CH9, and wild-type LmRXR, each with the optimization sequence AACAATGGA.
Figure 7A:
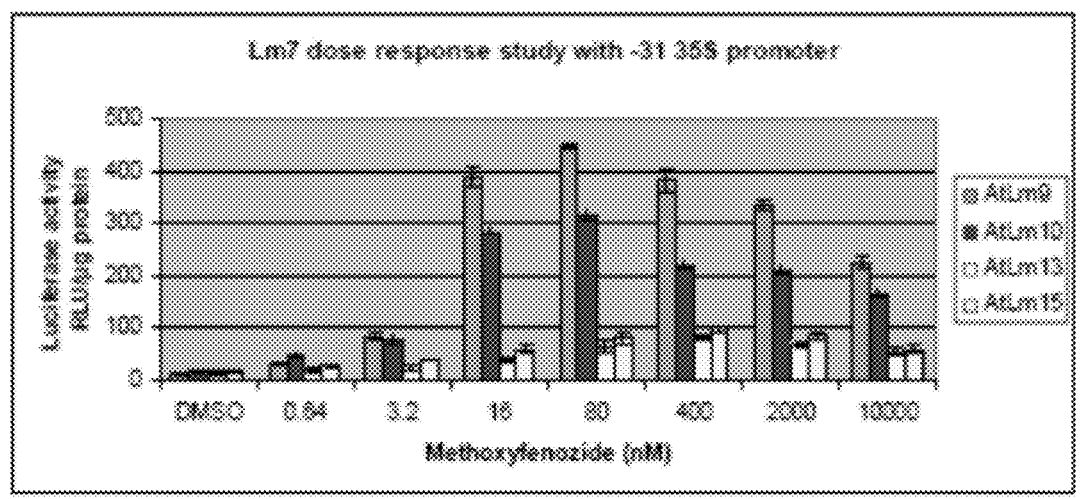
FIGS. 7A-7D are bar graphs comparing dose-response to ligand in T2 *Arabidopsis* plants including containing EcR gene switches containing the Lm-7 LmRXR mutant (FIGS. 7A and 7B), wild-type LmRXR (FIG. 7C), and CH9 (FIG. 7D).
Figure 7B:
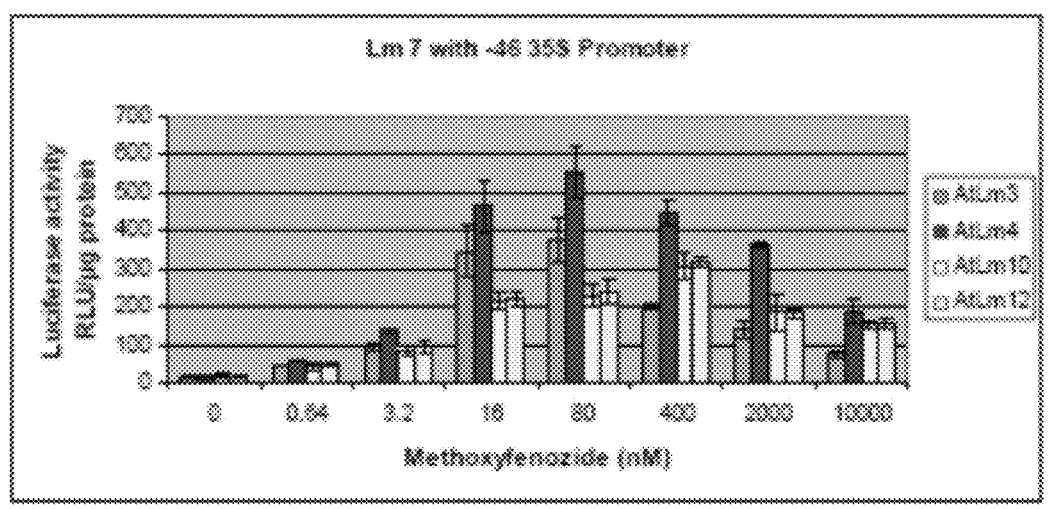
Figure 7C:
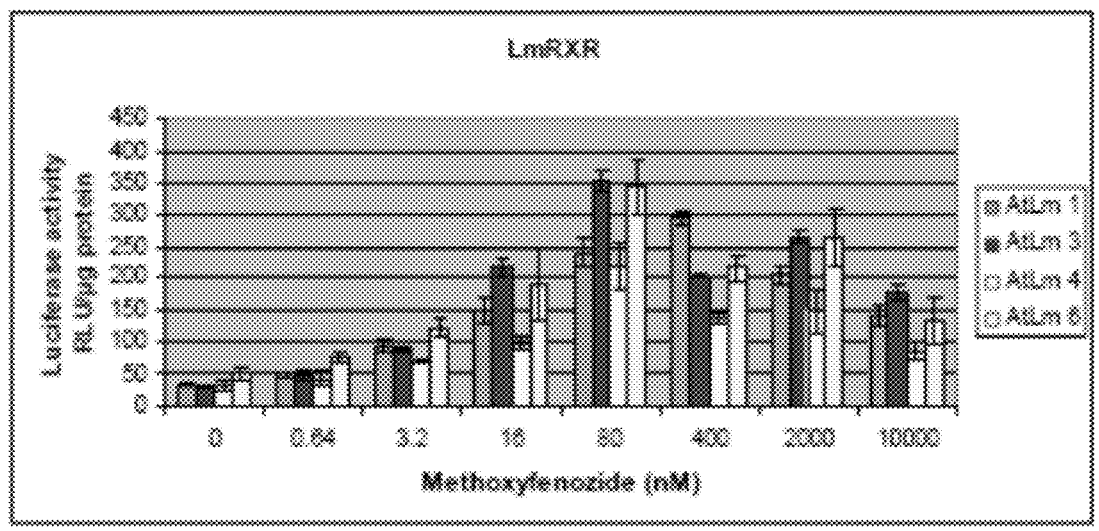
Figure 7D:
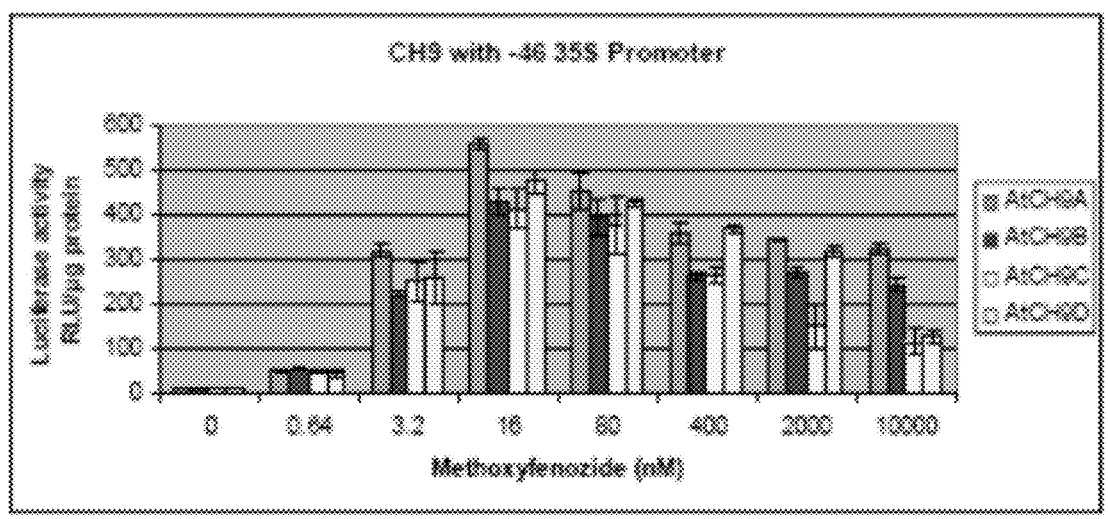

Optimization of translational start site: Several translational optimization sequences were tested for better transgene expression in plants, upstream to the luciferase reporter gene translational start site. Among several sequences tested, the AACAATGG sequence was particularly selected for enhancing induction of luciferase activity (FIG. 5). When this sequence was placed upstream to the luciferase reporter gene, induction of luciferase increased. The present inventors tested response of wild-type LmRXR and different LmRXR mutants in transient expression studies with luciferase having the translational optimization sequence and the present inventors found that induction of luciferase activity increased while background activity did not increase significantly compared to wild-type LmRXR (FIG. 6).

Comparison of luciferase induction levels by GCfE+VLm-1-Lm-7, GCfE+VLmRXR, GCfE+VCH9 in tobacco protoplasts: To compare ligand sensitivity and background expression levels of the luciferase reporter gene in the absence of ligand, combination of receptor constructs, pK80GCfE+ pK80VLm-1-Lm-7, pK80GCfE+pK80LmRXR, and pK80GCfE+VCH9 were electroporated into tobacco protoplasts. Electroporated protoplasts were exposed to various concentrations of methoxyfenozide and luciferase activity was quantified 24-h after addition of ligand. In tobacco protoplasts the background activity of the luciferase gene in the absence of ligand was similar in the case of the EcR gene switch containing Lm-7 and CH9 while background activity was significantly lower as compared to the EcR gene switch containing LmRXR (wt) (FIG. 6). In tobacco protoplasts, luciferase activity supported by the EcR gene switch containing Lm-7 (V123I:A62S:T81H) reaches maximum level at 80 nm methoxyfenozide while with CH9 maximum luciferase activity was observed at 16 nM concentration of ligand. Thus, the EcR gene switch containing Lm-7 triple mutant supported low background activity in the absence of ligand as well as high-ligand sensitivity and was chosen for further testing in stable expression studies in *Arabidopsis*. For stable transformation, GCfE+VLm-7 two-hybrid gene switch was cloned into T-DNA region of the pCAMBIA2300 binary vector. The transgenic plants developed for GCfE+VLmR, GCfE+ VLm7, GCfE+VCH9 two hybrid gene switch are designated as AtLm, AtLm7, and AtCH9.

Dose response study with T2 *Arabidopsis* plants: In order to analyze methoxyfenozide dose response, four *Arabidopsis* lines were analyzed for each construct. The T2 seeds were plated on agar medium supplemented with 50 mg/l kanamycin and 0 (DMSO), 0.64, 3.2, 16, 80, 400, 2000, 10,000 nM methoxyfenozide. After 20 days, three seedlings from each plate were collected and assayed separately for luciferase activity. AtLm-7 plants exhibited the low background expression in the absence of ligand and high luciferase activity similar to CH9 in the presence of 16-80 nM ligand while AtLm plants showed the higher background activity in the absence of ligand compared to AtLm-7 and CH9 (FIG. 7). Some variability in the levels of luciferase induced by methoxyfenozide was observed among the four lines tested. The results obtained with the stable transgenic plants also confirm the high-ligand sensitivity and low-background activity of the GCfE+VLm-7 gene switch observed in protoplasts.

Figure 8A:
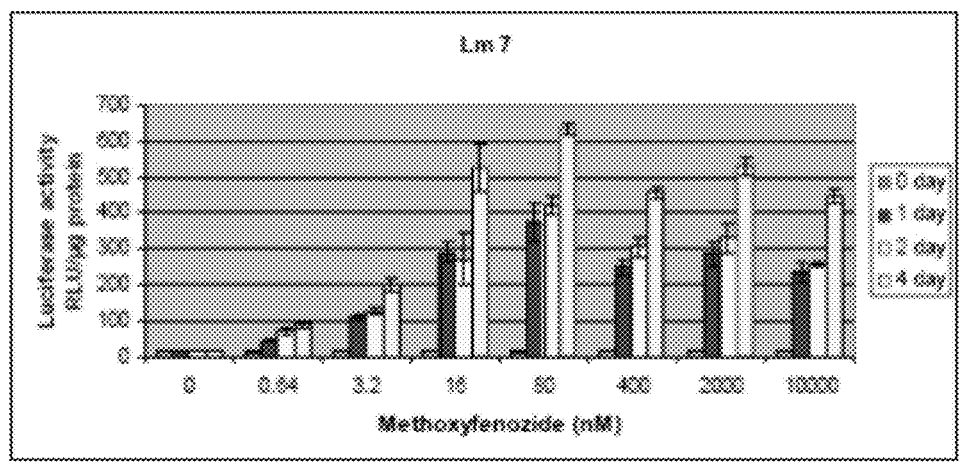
FIGS. 8A-8C area series of bar graphs from a time-course induction of luciferase gene activity in T2 *Arabidopsis* plants containing EcR gene switches containing the Lm-7 LmRXR mutant (FIG. 8A), CH9 (FIG. 8B), and wild-type LmRXR (FIG. 8C). Seedlings grown on agar medium without added methoxyfenozide were transferred to greenhouse. Different concentrations (0, 0.64, 3.2, 16, 80, 400, 2000, 10 000 nm) of ligand was applied to soil. Samples were collected at 0, 1, 2 and 4 days after addition of ligand and luciferase activity was measured in terms of RLU/μg protein.
Figure 8B:
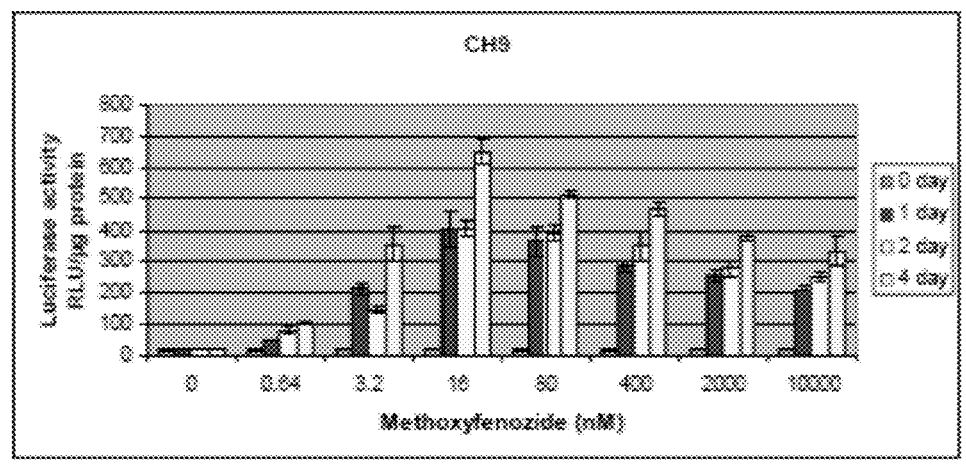
Figure 8C:
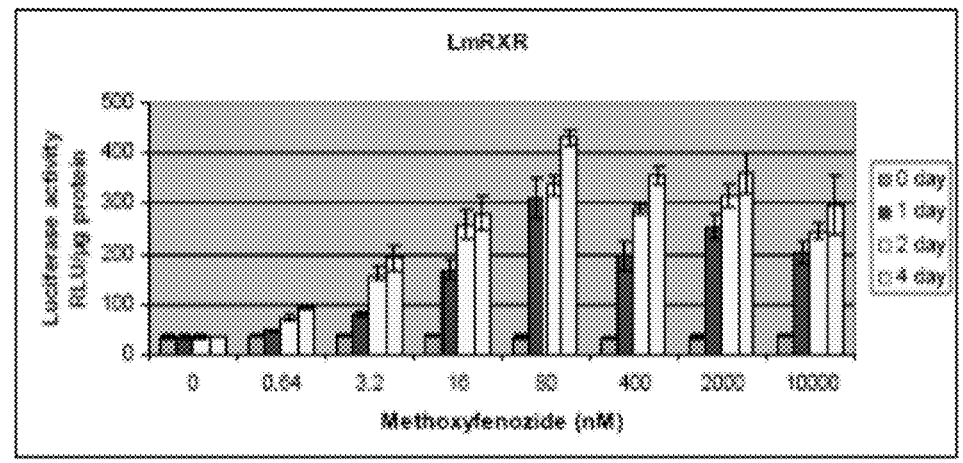

Time course study: In order to evaluate the regulation of the GCfE+VLm-7 two hybrid gene switch over time, T2 seeds collected from *Arabidopsis* transgenic line AtLm-7b were germinated on agar medium containing 50 mg/l kanamycin without methoxyfenozide. After 20 days, the seedlings were transferred to greenhouse and different concentrations of methoxyfenozide ligand was applied to soil. Luciferase reporter gene expression was monitored at 24-h intervals over 1, 2, and 4 days. As shown in FIG. 8, luciferase activity began to increase 24 h after application of ligand to soil and continues to increase up to 4 days. At most of the time points tested, the quantity of luciferase induction values observed were higher in the seedlings exposed to 16-80 nM methoxyfenozide (FIG. 8).

In the studies described in these examples, the present inventors have shown that the two-hybrid format switch containing certain LmRXR mutants as a partner of CfEcR supported high ligand sensitivity in the presence of low concentrations of ligand, and low levels of receptor gene activity in the absence of ligand. For example, the when the Lm-7 LmRXR mutant was used as a partner of CfEcR, the gene switch supported high ligand sensitivity in the presence of nanomolar concentration (16-80 nM) of ligand and low level of receptor gene activity in the absence of ligand compared to CH9 and wild-type LmRXR. These two features are probably the two most desirable characteristics that have limited the wide-spread use of the EcR gene switch.

The efficiency of two-hybrid gene switch containing Lm-7 mutant as partner of CfEcR in inducing luciferase reporter gene activity was also verified in stable transformation studies in *Arabidopsis* plant in dose response and time-course study experiments. Transgenic *Arabidopsis* lines tested showed low level of luciferase gene expression in the absence of ligand. There were some variations among the transgenic lines tested in terms of their response to the inducer concentrations applied. Except two lines Lm7c and Lm7d, all the transgenic lines analyzed showed maximum luciferase induction value in the presence of nanomolar concentration 16-80 nM concentration of methoxyfenozide.

Optimization of translation start site may also result in higher reporter activity. Taking into consideration of this fact, the present inventors tested several translational optimization sequences that were used to facilitate better transgene expression in plants, upstream to the luciferase reporter gene translation start site. The present inventors observed significant increase in the luciferase reporter gene activity in the presence of ligand when the AACAATGG sequence of was added to the upstream to the coding sequence of luciferase reporter gene while background activity was not increased significantly.

REFERENCES

Throughout this document, various references are mentioned. All such references are incorporated herein by reference, including the references set forth in the following list:

1) Ainley W M, Key J L (1990) Development of a heat shock inducible expression cassette for plants: characterization of parameters for its use in transient expression assays. Plant Mol Biol 14:949-967
2) Aoyama T, Chua N H (1997) A glucocorticoid-mediated transcriptional induction system in transgenic plants. Plant J 11:605-612
3) Bohner S, Lenk I I, Rieping M, Herold M, Gatz C (1999) Technical advance: transcriptional activator TGV mediates dexamethasone-inducible and tetracyclineinactivatable gene expression. Plant J 19:87-95
4) Bruce W, Folkerts O, Garnaat C, Crasta O, Roth B, Bowen B (2000) Expression profiling of the maize flavonoid pathway genes controlled by estradiolinducible transcription factors CRC and P. Plant Cell 12:65-80
5) Caddick M X, Greenland A J, Jepson I, Krause K P, Qu N, Riddell K V, Salter M G, Schuch W, Sonnewald U, Tomsett A B (1998) An ethanol inducible gene switch for plants used to manipulate carbon metabolism. Nat Biotechnol 16:177-180
6) Clough S J, Bent A F (1998) Floral dip: a simplified method for Agrobacterium-mediated transformation of *Arabidopsis thaliana*. Plant J 16:735-743
7) Gatz C (1996) Chemically inducible promoters in transgenic plants. Curr Opin Biotechnol 7:168-172
8) Gatz C, Frohberg C, Wendenburg R (1992) Stringent repression and homogeneous de-repression by tetracycline of a modified CaMV 35S promoter in intact transgenic tobacco plants. Plant J 2:397-404
9) Hare P D, Chua N H (2002) Excision of selectable marker genes from transgenic plants. Nat Biotechnol 20:575-580
10) Koo J C, Asurmendi S, Bick J, Woodford-Thomas T, Beachy R N (2004) Ecdysone agonist-inducible expression of a coat protein gene from tobacco mosaic virus confers viral resistance in transgenic Arabidopsis. Plant J 37:439-448
11) Lloyd A M, Schena M, Walbot V, Davis R W (1994) Epidermal cell fate determination in *Arabidopsis*: patterns defined by a steroid-inducible regulator. Science 266:436-439
12) Martinez A, Sparks C, Drayton P, Thompson J, Greenland A, Jepson I (1999a) Creation of ecdysone receptor chimeras in plants for controlled regulation of gene expression. Mol Gen Genet 261:546-552
13) Martinez A, Sparks C, Hart C A, Thompson J, Jepson I (1999b) Ecdysone agonist inducible transcription in transgenic tobacco plants. Plant J 19:97-106
14) Mett V L, Lochhead L P, Reynolds P H (1993) Copper controllable gene expression system for whole plants. Proc Natl Acad Sci USA 90:4567-4571
15) Padidam M, Gore M, Lu D L, Smirnova O (2003) Chemical-inducible, ecdysone receptor-based gene expression system for plants. Transgenic Res 12:101-109
16) Palli S R, Hormann R E, Schlattner U, Lezzi M (2005a) Ecdysteroid receptors and their applications in agriculture and medicine. Vitam Horm 73:59-100
17) Palli S R, Kapitskaya M Z, Potter D W (2005b) The influence of heterodimer partner ultraspiracle/retinoid X receptor on the function of ecdysone receptor. Febs J 272:5979-5990
18) Rieping M, Fritz M, Prat S, Gatz C (1994) A dominant negative mutant of PG13 suppresses transcription from a cauliflower mosaic virus 35S truncated promoter in transgenic tobacco plants. Plant Cell 6:1087-1098
19) Schena M, Lloyd A M, Davis R W (1991) A steroidinducible gene expression system for plant cells. Proc Natl Acad Sci USA 88:10421-10425
20) Tang W, Newton R J (2004) Regulated gene expression by glucocorticoids in cultured Virginia pine (Pinus virginiana Mill.) cells. J Exp Bot 55:1499-1508
21) Tavva V S, Dinkins R D, Palli S R, Collins G B (2006) Development of a methoxyfenozide-responsive gene switch for applications in plants. Plant J 45:457-469
22) Unger E, Cigan A M, Trimnell M, Xu R J, Kendall T, Roth B, Albertsen M (2002) A chimeric ecdysone receptor facilitates methoxyfenozide-dependent restoration of male fertility in ms45 maize. Transgenic Res 11:455-465
23) Weinmann P, Gossen M, Hillen W, Bujard H, Gatz C (1994) A chimeric transactivator allows tetracyclineresponsive gene expression in whole plants. Plant J 5:559-569
24) Wilde R J, Shufflebottom D, Cooke S, Jasinska I, Merryweather A, Beni R, Brammar W J, Bevan M, Schuch W (1992) Control of gene expression in tobacco cells using a bacterial operator-repressor system. Embo J 11:1251-1259
25) Williams S, Friedrich L, Dincher S, Carozzi N, Kessmann H (1992) Chemical regulation of *Bacillus thuringiensis*-endotoxin expression in transgenic plants. BioTechnology 10:540-543
26) Zuo J, Chua N H (2000) Chemical-inducible systems for regulated expression of plant genes. Curr Opin Biotechnol 11:146-151
27) Zuo J, Niu Q W, Chua N H (2000) Technical advance: an estrogen receptor-based transactivator XVE mediates highly inducible gene expression in transgenic plants. Plant J 24:265-273
28) Zuo J, Niu Q W, Moller S G, Chua N H (2001) Chemicalregulated, site-specific DNA excision in transgenic plants. Nat Biotechnol 19:157-161

What is claimed is:

1. A system for modulating expression of a gene-of-interest in a host plant cell, comprising:
   an EcR gene expression cassette comprising a first polynucleotide encoding a first polypeptide including
      a DNA binding domain that recognizes a response element associated with the gene-of-interest, and
      a ligand binding domain from an EcR;
   an RXR gene expression cassette comprising a second polynucleotide encoding a second polypeptide including,
      a transactivation domain, and
      a ligand binding domain of a modified RXR, comprising a polypeptide sequence of SEQ ID NO: 1 with an amino acid mutation selected from the group consisting of T94A; T81H; A62S; A62S:T81H; and A62S:T81H:V123I,
   wherein the first and second polypeptides dimerize in the presence of a ligand; and
   a gene-of-interest expression cassette for expressing the gene-of-interest in the host plant cell comprising
      the response element to which the DNA binding domain binds,
      a promoter that is activated by the transactivation domain, and
      the gene of interest,
   wherein expression of the gene-of-interest in the host plant cell is affected by applying the ligand.

2. The system according to claim 1, wherein the EcR ligand binding domain is a truncated EcR ligand binding domain.

3. The system according to claim 1, wherein the EcR ligand binding domain contains twelve helices.

4. The system according to claim 1, wherein the EcR ligand binding domain is a ligand binding domain selected from: a spruce budworm EcR, a moth EcR, a butterfly EcR, a fly EcR, a mosquito EcR, a beetle EcR, a locust EcR, a whitefly EcR, a fruit fly EcR, a hone bee EcR, and a leaf hopper EcR.

5. The system according to claim 1, wherein the EcR ligand binding is from a spruce budworm EcR.

6. The system according to claim 1, wherein the DNA-binding domain and the response element are selected from: GAL4 147 DNA-binding domain and response element; GAL4 65 DNA-binding domain and response element; GAL4 93 DNA-binding domain and response element; LexA DNA-binding domain and response element; and Lac repressor DNA-binding domain and response element.

7. The system according to claim 1, wherein the DNA-binding domain and the response element are GAL4 147 DNA-binding domain and response element.

8. The system of claim 1, wherein the amino acid mutation is T94A.

9. The system according to claim 1, wherein the RXR is a truncated RXR.

10. The system according to claim 1, wherein the ligand binding domain of the RXR is a ligand binding domain selected from: a migratory locust RXR, a mouse RXR, a honey bee RXR, a beetle RXR, a whitefly RXR, or a leaf hopper RXR.

11. The system of claim 1, wherein the ligand binding domain of the RXR is not from human RXR.

12. The system according to claim 1, wherein the ligand binding domain of the RXR is from a migratory locust RXR.

13. The system according to claim 1, wherein the transactivation domain is selected from: a VP16 activation domain; a GAL4 activation domain, a p53 activation domain, and a p65 subunit of Nf-kb activation domain.

14. The system according to claim 1, wherein the transactivation domain is a VP16 activation domain.

15. The system according to claim 1, wherein the EcR gene expression cassette and the RXR gene expression cassette are under the control of constitutive promoters.

16. The system according to claim 15, wherein the constitutive promoters are selected from the group consisting of: 35S promoters; CaMv promoters; and CSV promoters.

17. The system according to claim 15, wherein the constitutive promoters of the EcR gene expression cassette and the RXR gene expression cassette are 35S promoters.

18. The system of claim 1, wherein the gene-of-interest expression cassette further includes a translational optimization sequence.

19. The system of claim 18, wherein the translational optimization sequence comprises the sequence AACAATGGA.

20. The system according to claim 1, wherein the promoter of the gene-of-interest expression cassette is selected from: −46 35S promoter; or TATAA promoter.

21. The system according to claim 20, wherein the promoter of the gene-of-interest expression cassette is −46 35S promoter.

22. The system according to claim 1, wherein the ligand is selected from: a diacylhydrazine compound, methoxyfenozide, tubefenozide, halofenozide, and chromogenozide.

23. The system according to claim 22, wherein the ligand is methoxyfenozide.

24. The system according to claim 23, wherein the concentration of ligand for expressing the gene-of-interest is about 15 nM to about 100 nM.

25. A method of modulating expression of a gene-of-interest in a host plant cell, comprising:
(1) introducing into the host plant cell a system having
(a) an EcR gene expression cassette for expressing a first polypeptide, including
(i) a binding domain that recognizes a response element associated with the gene-of-interest, and
(ii) a ligand binding domain from an EcR; and
(b) an RXR gene expression cassette for expressing a second polypeptide, including
(i) a transactivation domain, and
(ii) a ligand binding domain of a modified RXR, comprising a polypeptide sequence of SEQ ID NO: 1 with an amino acid mutation selected from the group consisting of: T94A; T81H; A62S; A62S:T81H; and A62S:T81H:V123I; and
(c) a gene-of-interest expression cassette, including
(i) the response element to which the binding domain binds,
(ii) a promoter that is activated by the transactivation domain, and
(iii) the gene of interest; and
(2) introducing into the host plant cell a ligand that binds the ligand-binding domain of the first polypeptide.

26. The method of claim 25, wherein the gene-of-interest expression cassette further includes a translational optimization sequence.

27. The system of claim 26, wherein the translational optimization sequence comprises the sequence AACAATGGA.

28. An isolated molecule selected from the group consisting of:
an isolated nucleic acid comprising a sequence that encodes a polypeptide comprising SEQ ID NO: 1 with an amino acid mutation selected from the group consisting of: T94A; T81H; A62S; A62S:T81H; and A62S:T81H:V123I; and
an isolated polypeptide comprising SEQ ID NO: 1 with an amino acid mutation selected from the group consisting of: T94A; T81H; A62S; A62S:T81H; and A62S:T81H:V123I.

29. The isolated molecule of claim 28, wherein the amino acid mutation is T94A.

30. The system of claim 28, wherein the amino acid mutation is T81H.

31. The system of claim 28, wherein the amino acid mutation is A62S.

32. The system of claim 28, wherein the amino acid mutation is A62S:T81H.

33. The system of claim 28, wherein the amino acid mutation is A62S:T81H:V123I.

34. The system of claim 1, wherein the amino acid mutation is T81H.

35. The system of claim 1, wherein the amino acid mutation is A62S.

36. The system of claim 1, wherein the amino acid mutation is A62S:T81H.

37. The system of claim 1, wherein the amino acid mutation is A62S:T81H:V123I.

* * * * *

SEQUENCE LISTING

<160> NUMBER OF SEQ ID NOS: 16

<210> SEQ ID NO 1
<211> LENGTH: 129
<212> TYPE: PRT
<213> ORGANISM: Locusta migratoria

<400> SEQUENCE: 1

Leu His Thr Asp Met Pro Val Glu Arg Ile Leu Glu Ala Glu Lys Arg
1               5                   10                  15

Val Glu Cys Lys Ala Glu Asn Gln Val Glu Tyr Glu Leu Val Glu Trp
            20                  25                  30

Ala Lys His Ile Pro His Phe Thr Ser Leu Pro Leu Glu Asp Gln Val
        35                  40                  45

Leu Leu Leu Arg Ala Gly Trp Asn Glu Leu Leu Ile Ala Ala Phe Ser
    50                  55                  60

His Arg Ser Val Asp Val Lys Asp Gly Ile Val Leu Ala Thr Gly Leu
65                  70                  75                  80

Thr Val His Arg Asn Ser Ala His Gln Ala Gly Val Gly Thr Ile Phe
                85                  90                  95

Asp Arg Val Leu Thr Glu Leu Val Ala Lys Met Arg Glu Met Lys Met
            100                 105                 110

Asp Lys Thr Glu Leu Gly Cys Leu Arg Ser Val Ile Leu Phe Asn Pro
        115                 120                 125

Glu

<210> SEQ ID NO 2
<211> LENGTH: 35
<212> TYPE: DNA
<213> ORGANISM: Artificial Sequence
<220> FEATURE:
<223> OTHER INFORMATION: Primer

<400> SEQUENCE: 2
cttggctgct tgcgagctgt tattcttttc aatcc                          35

<210> SEQ ID NO 3
<211> LENGTH: 35
<212> TYPE: DNA
<213> ORGANISM: Artificial Sequence
<220> FEATURE:
<223> OTHER INFORMATION: Primer

<400> SEQUENCE: 3
ggattgaaaa gaataacagc tcgcaagcag ccaag                          35

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
ttgacagaac tggtatcaaa gatgagagaa atg                            33

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5

```
catttctctc atctttgata ccagttctgt caa                                    33

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
caagctggag tcggcgcaat atttgacaga gttttg                                 36

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
caaaactctg tcaaatattg cgccgactcc agcttg                                 36

<210> SEQ ID NO 8
<211> LENGTH: 36
<212> TYPE: DNA
<213> ORGANISM: Artificial Sequence
<220> FEATURE:
<223> OTHER INFORMATION: Primer

<400> SEQUENCE: 8
cttgccactg gtctccacgt gcatcgaaat tctgcc                                 36

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
ggcagaattt cgatgcacgt ggagaccagt ggcaa                                  35

<210> SEQ ID NO 10
<211> LENGTH: 34
<212> TYPE: DNA
<213> ORGANISM: Artificial Sequence
<220> FEATURE:
<223> OTHER INFORMATION: Primer

<400> SEQUENCE: 10
gaactgctaa ttgcatcatt ttcacatcga tctg                                   34

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
cagatcgatg tgaaaatgat gcaattagca gttc                                   34
```

```
<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
tggctgcttg cgatctatta ttcttttcaa tcc                               33

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
ggattgaaaa gaatagatcg caagcagcca                                   30

<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14
ctcgagaaaa atggaagacg ccaaaaacat aaag                              34

<210> SEQ ID NO 15
<211> LENGTH: 34
<212> TYPE: DNA
<213> ORGANISM: Artificial Sequence
<220> FEATURE:
<223> OTHER INFORMATION: Primer

<400> SEQUENCE: 15
ctcgagaacc atggaagacg ccaaaaacat aaag                              34

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
ctcgagaaca atggaagacg ccaaaaacat aaag                              34
```